US006849723B2

(12) United States Patent
Cook et al.

(10) Patent No.: US 6,849,723 B2
(45) Date of Patent: Feb. 1, 2005

(54) OLIGONUCLEOTIDE ANALOGS HAVING MODIFIED DIMERS

(75) Inventors: Phillip Dan Cook, Lake San Marcos, CA (US); Muthiah Manoharan, Carlsbad, CA (US); Balkrishen Bhat, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/195,211

(22) Filed: Jul. 15, 2002

(65) Prior Publication Data

US 2003/0181693 A1 Sep. 25, 2003

Related U.S. Application Data

(63) Continuation of application No. 09/131,102, filed on Aug. 7, 1998, now Pat. No. 6,420,549, which is a continuation-in-part of application No. 08/848,840, filed on Apr. 30, 1997, now Pat. No. 5,965,722, which is a continuation-in-part of application No. 08/468,037, filed on Jun. 6, 1995, now Pat. No. 5,859,221.

(51) Int. Cl.$^7$ .................... C07H 21/00; C07H 21/02; C07H 21/04
(52) U.S. Cl. .................... 536/22.1; 536/23.1; 536/24.3; 536/25.3
(58) Field of Search ................ 536/23.1, 22.1, 536/25.3, 24.3

(56) References Cited

U.S. PATENT DOCUMENTS

| | | | |
|---|---|---|---|
| 3,687,808 A | 8/1972 | Merigan et al. ............. 195/28 |
| 4,426,330 A | 1/1984 | Sears ........................ 260/403 |
| 4,469,863 A | 9/1984 | Ts'o et al. ................... 536/27 |
| 4,476,301 A | 10/1984 | Imbach et al. .............. 536/27 |
| 4,534,899 A | 8/1985 | Sears ........................ 260/403 |
| 4,587,044 A | 5/1986 | Miller et al. ............... 530/211 |
| 4,605,735 A | 8/1986 | Miyoshi et al. ............. 536/27 |
| 4,667,025 A | 5/1987 | Miyoshi et al. ............. 536/27 |
| 4,762,779 A | 8/1988 | Snitman ...................... 435/6 |
| 4,789,737 A | 12/1988 | Miyoshi et al. ............. 536/27 |
| 4,824,941 A | 4/1989 | Gordon et al. ............. 530/403 |
| 4,828,979 A | 5/1989 | Klevan et al. ............... 435/6 |
| 4,835,263 A | 5/1989 | Nguyen et al. ............. 536/27 |
| 4,845,205 A | 7/1989 | Huynh Dinh et al. ....... 536/27 |
| 4,876,335 A | 10/1989 | Yammane et al. ........... 536/27 |
| 4,904,582 A | 2/1990 | Tullis ......................... 435/6 |
| 4,948,882 A | 8/1990 | Ruth .......................... 536/27 |
| 4,958,013 A | 9/1990 | Letsinger .................... 536/27 |
| 5,013,556 A | 5/1991 | Woodle et al. ............. 424/450 |
| 5,023,243 A | 6/1991 | Tullis ......................... 514/44 |
| 5,034,506 A | 7/1991 | Summerton et al. ........ 528/391 |
| 5,082,830 A | 1/1992 | Brakel et al. .............. 514/44 |
| 5,108,921 A | 4/1992 | Low et al. ............... 435/240.1 |
| 5,109,124 A | 4/1992 | Ramachandran et al. ..... 536/27 |
| 5,112,963 A | 5/1992 | Pieles et al. ................ 536/27 |
| 5,118,802 A | 6/1992 | Smith et al. ................ 536/27 |
| 5,130,302 A | 7/1992 | Spielvogel et al. .......... 514/45 |
| 5,134,066 A | 7/1992 | Rogers et al. ............... 435/91 |
| 5,138,045 A | 8/1992 | Cook et al. ................. 536/27 |
| 5,149,797 A | 9/1992 | Pederson et al. ........... 536/27 |
| 5,166,315 A | 11/1992 | Summerton et al. ........ 528/406 |
| 5,175,273 A | 12/1992 | Bischofberger et al. ..... 536/27 |
| 5,177,198 A | 1/1993 | Spielvogel et al. ....... 536/25.33 |
| 5,185,444 A | 2/1993 | Summerton et al. ......... 544/81 |
| 5,188,897 A | 2/1993 | Suhadolnik et al. ...... 428/402.2 |
| 5,212,295 A | 5/1993 | Cook ....................... 536/26.7 |
| 5,213,804 A | 5/1993 | Martin et al. ............. 424/450 |
| 5,214,134 A | 5/1993 | Weis et al. ............... 536/25.3 |
| 5,214,136 A | 5/1993 | Lin et al. ................... 514/44 |
| 5,216,141 A | 6/1993 | Benner .................... 536/27.13 |
| 5,218,105 A | 6/1993 | Cook et al. .............. 536/25.31 |
| 5,220,007 A | 6/1993 | Pederson et al. .......... 536/23.1 |
| 5,227,170 A | 7/1993 | Sullivan .................... 424/450 |
| 5,235,033 A | 8/1993 | Summerton et al. ........ 528/391 |
| 5,245,022 A | 9/1993 | Weis et al. ............... 536/24.5 |
| 5,254,469 A | 10/1993 | Warren, III et al. ........ 435/188 |
| 5,256,775 A | 10/1993 | Froehler ................... 536/25.6 |
| 5,258,506 A | 11/1993 | Urdea ...................... 536/23.1 |
| 5,262,536 A | 11/1993 | Hobbs, Jr. .................. 546/25 |
| 5,264,423 A | 11/1993 | Cohen et al. ............... 514/44 |
| 5,264,562 A | 11/1993 | Matteucci .................. 536/23.1 |
| 5,264,564 A | 11/1993 | Matteucci .................. 536/23.1 |
| 5,272,250 A | 12/1993 | Spielvogel et al. ......... 530/300 |
| 5,276,019 A | 1/1994 | Cohen et al. ............... 514/44 |
| 5,278,302 A | 1/1994 | Caruthers et al. .......... 536/24.5 |
| 5,286,717 A | 2/1994 | Cohen et al. ............... 514/44 |
| 5,292,873 A | 3/1994 | Rokita et al. .............. 536/24.3 |
| 5,317,098 A | 5/1994 | Shizuya et al. ............ 536/23.1 |
| 5,321,131 A | 6/1994 | Agrawal et al. ........... 536/25.34 |
| 5,354,844 A | 10/1994 | Beug et al. ................ 530/345 |
| 5,356,633 A | 10/1994 | Woodle et al. ............ 424/450 |
| 5,366,878 A | 11/1994 | Pederson et al. .......... 435/91.3 |
| 5,367,066 A | 11/1994 | Urdea et al. .............. 536/24.3 |
| 5,371,241 A | 12/1994 | Brush et al. .............. 549/220 |
| 5,378,825 A * | 1/1995 | Cook et al. .............. 536/25.34 |
| 5,391,723 A | 2/1995 | Priest ...................... 536/53.1 |
| 5,395,619 A | 3/1995 | Zalipsky et al. .......... 424/450 |
| 5,399,676 A | 3/1995 | Froehler .................. 536/23.1 |

(List continued on next page.)

FOREIGN PATENT DOCUMENTS

| | | |
|---|---|---|
| WO | WO 92/05186 | 4/1992 |
| WO | WO 94/02501 | 2/1994 |
| WO | WO 94/26764 | 11/1994 |

OTHER PUBLICATIONS

Neilson et al. Journal of the American Chemical Society 96:7, Apr. 3, 1974.*

(List continued on next page.)

Primary Examiner—Jezia Riley
(74) Attorney, Agent, or Firm—Isis Patent Department

(57) ABSTRACT

Modified dimers having a ribose sugar moiety in the 5' nucleoside and a 2' modified sugar in the 3' nucleoside are provided. The modified dimers are useful in the preparation of oligonucleotide analogs having enhanced properties compared to native oligonucleotides, including increased nuclease resistance, enhanced binding affinity and improved protein binding.

14 Claims, No Drawings

U.S. PATENT DOCUMENTS

| | | | |
|---|---|---|---|
| 5,403,711 A | 4/1995 | Walder et al. | 435/6 |
| 5,405,938 A | 4/1995 | Summerton et al. | 528/406 |
| 5,405,939 A | 4/1995 | Suhadolnik et al. | 530/322 |
| 5,414,077 A | 5/1995 | Lin et al. | 536/24.3 |
| 5,416,016 A | 5/1995 | Low et al. | 435/240.1 |
| 5,416,203 A | 5/1995 | Letsinger | 536/25.34 |
| 5,417,978 A | 5/1995 | Tari et al. | 424/450 |
| 5,432,272 A | 7/1995 | Benner | 536/25.3 |
| 5,434,257 A | 7/1995 | Matteucci et al. | 536/24.3 |
| 5,451,463 A | 9/1995 | Nelson et al. | 428/402 |
| 5,453,496 A | 9/1995 | Caruthers et al. | 536/24.5 |
| 5,455,233 A | 10/1995 | Spielvogel et al. | 514/44 |
| 5,457,187 A | 10/1995 | Gmeiner et al. | 536/25.5 |
| 5,459,127 A | 10/1995 | Felgner et al. | 514/7 |
| 5,459,255 A | 10/1995 | Cook et al. | 536/27.13 |
| 5,462,854 A | 10/1995 | Coassin et al. | 435/6 |
| 5,466,677 A | 11/1995 | Baxter et al. | 514/44 |
| 5,469,854 A | 11/1995 | Unger et al. | 128/662.02 |
| 5,470,967 A | 11/1995 | Huie et al. | 536/24.3 |
| 5,484,908 A | 1/1996 | Froehler et al. | 536/24.31 |
| 5,486,603 A | 1/1996 | Buhr | 536/24.3 |
| 5,489,677 A | 2/1996 | Sanghvi et al. | 536/22.1 |
| 5,491,133 A | 2/1996 | Walder et al. | 514/44 |
| 5,502,177 A | 3/1996 | Matteucci et al. | 536/26.6 |
| 5,510,475 A | 4/1996 | Agrawal et al. | 536/24.3 |
| 5,512,295 A | 4/1996 | Kornberg et al. | 424/450 |
| 5,512,439 A | 4/1996 | Hornes et al. | 435/6 |
| 5,512,667 A | 4/1996 | Reed et al. | 536/24.31 |
| 5,514,785 A | 5/1996 | Van Ness et al. | 536/22.1 |
| 5,519,126 A | 5/1996 | Hecht | 536/24.3 |
| 5,521,291 A | 5/1996 | Curiel et al. | 530/391.7 |
| 5,525,465 A | 6/1996 | Haralambidis et al. | 435/6 |
| 5,525,711 A | 6/1996 | Hawkins et al. | 536/22.1 |
| 5,527,528 A | 6/1996 | Allen et al. | 424/178.1 |
| 5,534,259 A | 7/1996 | Zalipsky et al. | 424/450 |
| 5,536,821 A | 7/1996 | Agrawal et al. | 536/22.1 |
| 5,541,306 A | 7/1996 | Agrawal et al. | 536/22.1 |
| 5,541,307 A | 7/1996 | Cook et al. | 536/23.1 |
| 5,541,313 A | 7/1996 | Ruth | 536/24.3 |
| 5,543,152 A | 8/1996 | Webb et al. | 424/150 |
| 5,543,158 A | 8/1996 | Gref et al. | 424/501 |
| 5,545,730 A | 8/1996 | Urdea et al. | 536/28.51 |
| 5,547,932 A | 8/1996 | Curiel et al. | 435/65 |
| 5,550,111 A | 8/1996 | Suhadolnik et al. | 514/44 |
| 5,552,538 A | 9/1996 | Urdea et al. | 536/24.3 |
| 5,552,540 A | 9/1996 | Haralambidis | 536/25.34 |
| 5,556,948 A | 9/1996 | Tagawa et al. | 530/391.9 |
| 5,561,225 A | 10/1996 | Maddry et al. | 536/23.1 |
| 5,563,253 A | 10/1996 | Agrawal et al. | 536/222.1 |
| 5,565,350 A | 10/1996 | Kmiec | 435/172.3 |
| 5,565,552 A | 10/1996 | Magda et al. | 534/11 |
| 5,567,810 A | 10/1996 | Weis et al. | 536/25.3 |
| 5,571,799 A | 11/1996 | Tkachuk et al. | 514/47 |
| 5,574,142 A | 11/1996 | Meyer, Jr. et al. | 536/23.1 |
| 5,578,717 A | 11/1996 | Urdea et al. | 536/26.1 |
| 5,578,718 A | 11/1996 | Cook et al. | 536/27.21 |
| 5,580,020 A | 12/1996 | Catchings | 435/172.3 |
| 5,580,575 A | 12/1996 | Unger et al. | 424/450 |
| 5,580,731 A | 12/1996 | Chang et al. | 435/6 |
| 5,585,481 A | 12/1996 | Arnold, Jr. et al. | 536/25.33 |
| 5,587,361 A | 12/1996 | Cook et al. | 514/44 |
| 5,587,371 A | 12/1996 | Sessler et al. | 514/185 |
| 5,587,469 A | 12/1996 | Cook et al. | 536/23.1 |
| 5,591,584 A | 1/1997 | Chang et al. | 435/6 |
| 5,591,721 A | 1/1997 | Agrawal et al. | 514/44 |
| 5,594,121 A | 1/1997 | Froehler et al. | 536/23.5 |
| 5,595,726 A | 1/1997 | Magda et al. | 424/9.61 |
| 5,595,756 A | 1/1997 | Bally et al. | 424/450 |
| 5,596,086 A | 1/1997 | Matteucci et al. | 536/22.1 |
| 5,596,091 A | 1/1997 | Switzer | 536/24.5 |
| 5,597,696 A | 1/1997 | Linn et al. | 435/6 |
| 5,599,923 A | 2/1997 | Sessler et al. | 540/145 |
| 5,599,928 A | 2/1997 | Hemmi et al. | 540/474 |
| 5,602,240 A | 2/1997 | De Mesmaeker et al. | 536/23.1 |
| 5,608,046 A | 3/1997 | Cook et al. | 536/23.1 |
| 5,610,289 A | 3/1997 | Cook et al. | 536/25.34 |
| 5,614,617 A | 3/1997 | Cook et al. | 536/23.1 |
| 5,618,704 A | 4/1997 | Sanghvi et al. | 435/91.5 |
| 5,623,065 A | 4/1997 | Cook et al. | 536/23.1 |
| 5,623,070 A | 4/1997 | Cook et al. | 536/27.6 |
| 5,625,050 A | 4/1997 | Beaton et al. | 536/24.1 |
| 5,633,360 A | 5/1997 | Bischofberger et al. | 536/22.1 |
| 5,652,356 A | 7/1997 | Agrawal | 536/24.5 |
| 5,663,312 A | 9/1997 | Chaturvedula | 536/22.1 |
| 5,677,437 A | 10/1997 | Teng et al. | 536/23.1 |
| 5,677,439 A | 10/1997 | Weis et al. | 536/23.1 |
| 5,681,941 A | 10/1997 | Cook et al. | 536/23.1 |
| 5,688,941 A | 11/1997 | Cook et al. | 536/25.3 |
| 5,697,248 A | 12/1997 | Brown | 73/290 |
| 5,700,922 A | 12/1997 | Cook | 536/23.1 |
| 5,750,692 A | 5/1998 | Cook et al. | 544/253 |
| 5,898,031 A | 4/1999 | Crooke | 435/172.3 |
| 5,955,589 A | 9/1999 | Cook et al. | 536/23.1 |
| 6,420,549 B1 * | 7/2002 | Cook et al. | 536/24.2 |

OTHER PUBLICATIONS

Pitulle et al. Gene, 112 (1992) 101–105.*

Cheng et al. Biopolymers 1984, 22(5), pp. 1427–1444, abstract only.*

Catlin et al. Biopolymers 1975 14(1) pp. 51–72, abstract only.*

Beaucage, S.L. et al., "Advances in the Synthesis of Oligonucleotides by the Phosphoramidite Approach", *Tetrahedron*, 1992, 48, 2223–2311.

Fiandor, J. et al., "Synthesis of 3'–Deoxy-3'(2–Propynyl) Thymidine and 3'–Cyanomethyl-3'–Deoxythymidine, Analogs of AZT", *Tetrahedron Letts.*, 1990, 31, 597–600.

Greene and Wuts, Protective Groups in Organic Synthesis, $2^{nd}$ edition, John Wiley & Sons, New York, 1991.

Saison–Behmoaras, T. et al., "Short modified antisense oligonucleotides directed against Ha–*ras* point mutation induce selective cleavage of the mRNA and inhibit T24 cells proliferation", *EMBO J.*, 1991, 10, 1111–1118.

Uhlmann, E. et al., "Antisense Oligonucleotides: A New Therapeutic Principle," *Chem. Reviews*, 1990, 90, 543–584.

* cited by examiner

SEQUENCE LISTING

```
<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: Methylene (methylimino) backbone, ribose sugar
      moiety
<220> FEATURE:
<221> NAME/KEY: misc_feature
<222> LOCATION: (10)..(10)
<223> OTHER INFORMATION: 2'-O-CH3 Ribose sugar moiety

<400> SEQUENCE: 1
ctcgtaccTT tccggtcc                                                    18
```

```
<210> SEQ ID NO 2
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: Methylene (methylimino) backbone, 2'-O-CH3
      ribose sugar moiety
<220> FEATURE:
<221> NAME/KEY: misc_feature
<222> LOCATION: (10)..(10)
<223> OTHER INFORMATION: 2'-O-CH3 Ribose sugar moiety

<400> SEQUENCE: 2 ctcgtaccttt tccggtcc                                              18

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: Methylene (methylimino) backbone, ribose sugar
      moiety
<220> FEATURE:
<221> NAME/KEY: misc_feature
<222> LOCATION: (10)..(10)
<223> OTHER INFORMATION: Ribose sugar moiety

<400> SEQUENCE: 3 ctcgtaccttt tccggtcc                                              18

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: Methylene (methylimino) backbone, ribose sugar
      moiety
<220> FEATURE:
<221> NAME/KEY: misc_feature
<222> LOCATION: (9)..(9)
<223> OTHER INFORMATION: 2'-O-CH3 Ribose sugar moiety
<220> FEATURE:
<221> NAME/KEY: misc_feature
<222> LOCATION: (10)..(10)
<223> OTHER INFORMATION: Methylene (methylimino) backbone, ribose sugar
      moiety
<220> FEATURE:
<221> NAME/KEY: misc_feature
<222> LOCATION: (11)..(11)
<223> OTHER INFORMATION: 2'-O-CH3 Ribose sugar moiety

<400> SEQUENCE: 4 ctcgtactttt tccggtcc                                              18

<210> SEQ ID NO 5
<211> LENGTH: 18
<212> TYPE: DNA
<213> ORGANISM: Artificial Sequence
<220> FEATURE:
```

```
<223> OTHER INFORMATION: Oligonucleotide
<220> FEATURE:
<221> NAME/KEY: misc_feature
<222> LOCATION: (8)..(8)
<223> OTHER INFORMATION: Methylene (methylimino) backbone, 2'-O-CH3
      ribose sugar moiety
<220> FEATURE:
<221> NAME/KEY: misc_feature
<222> LOCATION: (9)..(9)
<223> OTHER INFORMATION: 2'-O-CH3 ribose sugar moiety
<220> FEATURE:
<221> NAME/KEY: misc_feature
<222> LOCATION: (10)..(10)
<223> OTHER INFORMATION: Methylene (methylimino) backbone, 2'-O-CH3
      ribose sugar moiety
<220> FEATURE:
<221> NAME/KEY: misc_feature
<222> LOCATION: (11)..(11)
<223> OTHER INFORMATION: 2'-O-CH3 ribose sugar moiety

<400> SEQUENCE: 5 ctcgtactt  tccggtcc                                               18

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: Methylene (methylimino) backbone, ribose sugar
      moiety
<220> FEATURE:
<221> NAME/KEY: misc_feature
<222> LOCATION: (9)..(9)
<223> OTHER INFORMATION: Ribose sugar moiety
<220> FEATURE:
<221> NAME/KEY: misc_feature
<222> LOCATION: (10)..(10)
<223> OTHER INFORMATION: Methylene (methylimino) backbone, ribose sugar
      moiety
<220> FEATURE:
<221> NAME/KEY: misc_feature
<222> LOCATION: (11)..(11)
<223> OTHER INFORMATION: Ribose sugar moiety

<400> SEQUENCE: 6 ctcgtactt  tccggtcc                                               18

<210> SEQ ID NO 7
<211> LENGTH: 16
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: Methylene (methylimino) backbone, ribose sugar
      moiety
<220> FEATURE:
<221> NAME/KEY: misc_feature
<222> LOCATION: (5)..(5)
<223> OTHER INFORMATION: 2'-O-CH3 Ribose sugar moiety
<220> FEATURE:
<221> NAME/KEY: misc_feature
<222> LOCATION: (6)..(6)
<223> OTHER INFORMATION: Methylene (methylimino) backbone, ribose sugar
      moiety
<220> FEATURE:
<221> NAME/KEY: misc_feature
<222> LOCATION: (7)..(7)
<223> OTHER INFORMATION: 2'-O-CH3 Ribose sugar moiety
```

```
<220> FEATURE:
<221> NAME/KEY: misc_feature
<222> LOCATION: (8)..(8)
<223> OTHER INFORMATION: Methylene (methylimino) backbone, ribose sugar
      moiety
<220> FEATURE:
<221> NAME/KEY: misc_feature
<222> LOCATION: (9)..(9)
<223> OTHER INFORMATION: 2'-O-CH3 Ribose sugar moiety
<220> FEATURE:
<221> NAME/KEY: misc_feature
<222> LOCATION: (10)..(10)
<223> OTHER INFORMATION: Methylene (methylimino) backbone, ribose sugar
      moiety
<220> FEATURE:
<221> NAME/KEY: misc_feature
<222> LOCATION: (11)..(11)
<223> OTHER INFORMATION: 2'-O-CH3 Ribose sugar moiety
<220> FEATURE:
<221> NAME/KEY: misc_feature
<222> LOCATION: (12)..(12)
<223> OTHER INFORMATION: Methylene (methylimino) backbone, ribose sugar
      moiety
<220> FEATURE:
<221> NAME/KEY: misc_feature
<222> LOCATION: (13)..(13)
<223> OTHER INFORMATION: 2'-O-CH3 Ribose sugar moiety

<400> SEQUENCE: 7 gcgtttttttt tttgcg                                                      16

<210> SEQ ID NO 8
<211> LENGTH: 16
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: Methylene (methylimino) backbone, 2'-O-CH3
      ribose sugar moiety
<220> FEATURE:
<221> NAME/KEY: misc_feature
<222> LOCATION: (5)..(5)
<223> OTHER INFORMATION: 2'-O-CH3 Ribose sugar moiety
<220> FEATURE:
<221> NAME/KEY: misc_feature
<222> LOCATION: (6)..(6)
<223> OTHER INFORMATION: Methylene (methylimino) backbone, 2'-O-CH3
      ribose sugar moiety
<220> FEATURE:
<221> NAME/KEY: misc_feature
<222> LOCATION: (7)..(7)
<223> OTHER INFORMATION: 2'-O-CH3 Ribose sugar moiety
<220> FEATURE:
<221> NAME/KEY: misc_feature
<222> LOCATION: (8)..(8)
<223> OTHER INFORMATION: Methylene (methylimino) backbone, 2'-O-CH3
      ribose sugar moiety
<220> FEATURE:
<221> NAME/KEY: misc_feature
<222> LOCATION: (9)..(9)
<223> OTHER INFORMATION: 2'-O-CH3 ribose sugar moiety
<220> FEATURE:
<221> NAME/KEY: misc_feature
<222> LOCATION: (10)..(10)
<223> OTHER INFORMATION: Methylene (methylimino) backbone, 2'-O-CH3
      ribose sugar moiety
<220> FEATURE:
<221> NAME/KEY: misc_feature
<222> LOCATION: (11)..(11)
```

```
<223> OTHER INFORMATION: 2'-O-CH3 Ribose sugar moiety
<220> FEATURE:
<221> NAME/KEY: misc_feature
<222> LOCATION: (12)..(12)
<223> OTHER INFORMATION: 2'-O-CH3 ribose sugar moiety
<220> FEATURE:
<221> NAME/KEY: misc_feature
<222> LOCATION: (13)..(13)
<223> OTHER INFORMATION: 2'-O-CH3 ribose sugar moiety

<400> SEQUENCE: 8
gcgttttttt tttgcg                                               16

<210> SEQ ID NO 9
<211> LENGTH: 16
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: Methylene (methylimino) backbone, 2'-O-CH3
      ribose sugar moiety
<220> FEATURE:
<221> NAME/KEY: misc_feature
<222> LOCATION: (5)..(5)
<223> OTHER INFORMATION: Ribose sugar moiety
<220> FEATURE:
<221> NAME/KEY: misc_feature
<222> LOCATION: (6)..(6)
<223> OTHER INFORMATION: Methylene (methylimino) backbone, ribose sugar
      moiety
<220> FEATURE:
<221> NAME/KEY: misc_feature
<222> LOCATION: (7)..(7)
<223> OTHER INFORMATION: Ribose sugar moiety
<220> FEATURE:
<221> NAME/KEY: misc_feature
<222> LOCATION: (8)..(8)
<223> OTHER INFORMATION: Methylene (methylimino) backbone, ribose sugar
      moiety
<220> FEATURE:
<221> NAME/KEY: misc_feature
<222> LOCATION: (9)..(9)
<223> OTHER INFORMATION: Ribose sugr moiety
<220> FEATURE:
<221> NAME/KEY: misc_feature
<222> LOCATION: (10)..(10)
<223> OTHER INFORMATION: Methylene (methylimino) backbone, ribose sugar
      moiety
<220> FEATURE:
<221> NAME/KEY: misc_feature
<222> LOCATION: (11)..(11)
<223> OTHER INFORMATION: Ribose sugar moiety
<220> FEATURE:
<221> NAME/KEY: misc_feature
<222> LOCATION: (12)..(12)
<223> OTHER INFORMATION: Methylene (methylimino) backbone, ribose sugar
      moiety
<220> FEATURE:
<221> NAME/KEY: misc_feature
<222> LOCATION: (13)..(13)
<223> OTHER INFORMATION: Ribose sugar moiety

<400> SEQUENCE: 9
gcgttttttt tttgcg                                               16
```

OLIGONUCLEOTIDE ANALOGS HAVING MODIFIED DIMERS

"This application is a continuation of 09/131,102, filed Aug. 7, 1998, now U.S. Pat. No. 6,420,549 which is a continuation in part of Ser. No. 08/848,840, filed Apr. 30, 1997, now U.S. Pat. No. 5,965,722, which is a continuation in part of Ser. No. 08/468,037, filed Jun. 6, 1995, now U.S. Pat. No. 5,859,221. The contents of each of the foregoing applications are incorporated herein by reference in their entirety.

FIELD OF THE INVENTION

The present invention relates to modified dimeric nucleoside compounds, oligonucleotide analogs prepared therefrom and methods of their use. In one aspect of the present invention, oligonucleotide analogs are provided that contain modified nucleoside dimers that enhance the hybridization of the oligonucleotide analogs to, for example, RNA. More specific objectives and advantages of the invention will hereinafter be made clear or become apparent to those skilled in the art during the course of explanation of preferred embodiments of the invention.

BACKGROUND OF THE INVENTION

It is well known that most of the bodily states in mammals, including most disease states, are affected by proteins. Classical therapeutic modes have generally focussed on interactions with such proteins in an effort to moderate their disease-causing or disease-potentiating functions. However, recently, attempts have been made to moderate the actual production of such proteins by interactions with molecules that direct their synthesis, such as intracellular RNA. By interfering with the production of proteins, maximum therapeutic effect and minimal side effects may be realized. It is the general object of such therapeutic approaches to interfere with or otherwise modulate gene expression leading to undesired protein formation.

One method for inhibiting specific gene expression is the use of oligonucleotides and oligonucleotide analogs. Certain oligonucleotide analogs have been accepted as therapeutic agents with great promise. Oligonucleotides and oligonucleotide analogs are known to hybridize to single-stranded DNA or RNA molecules. Hybridization is the sequence-specific base pair hydrogen bonding of nucleobases of the oligonucleotide or the oligonucleotide analog to the nucleobases of the target DNA or RNA molecule. Such nucleobase pairs are said to be complementary to one another.

In determining the extent of hybridization to a complementary nucleic acid, the relative ability of an oligonucleotide or an oligonucleotide analog to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

For use as therapeutics, oligonucleotides and oligonucleotide analogs must be transported across cell membranes or be taken up by cells, and appropriately hybridize to target DNA or RNA. These critical functions depend on the initial stability of the oligonucleotides toward nuclease degradation. A serious deficiency of unmodified oligonucleotides which affects their hybridization potential with target DNA or RNA for therapeutic purposes is the enzymatic degradation of administered oligonucleotides by a variety of intracellular and extracellular ubiquitous nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and resist nuclease degradation. The present invention describes the use of oligonucleotide analogs having modified dimers. These modified dimers have unexpectedly enhanced binding affinity when placed in an oligonucleotide.

While it has been recognized that nucleosides and oligonucleotides bearing base and sugar modifications are useful, there remains a long-felt need for oligonucleotides with greater binding affinity, hence improved hybridization characteristics, and greater nuclease resistance. Such oligonucleotides are desired as therapeutics, diagnostics, and research reagents.

SUMMARY OF THE INVENTION

The present invention presents modified dimeric nucleoside compounds having Formula I:

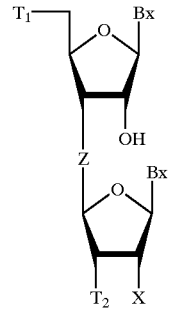

Formula I wherein

Z is a covalent intersugar linkage;

each $T_1$ and $T_2$ is, independently, —OH, —OR, —CH$_2$R, —NH(R), —SH, —SR, or a protected hydroxyl;

$B_X$ is a heterocyclic base;

X is F, O—R, S—R or N—R(R$_2$);

R is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;

and wherein any available hydrogen atom of said ring system is each replaceable with an alkoxy, alkylamino, urea or alkylurea group;

or R has one of the formulas:

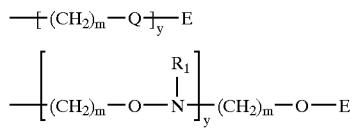

wherein

Q is O, S or $NR_2$;

m is from 1 to 10;

y is from 0 to 10;

E is $N(R_2)(R_3)$, $N=C(R_2)(R_3)$, $C_1-C_{10}$ alkyl, or $C_1-C_{10}$ substituted alkyl wherein said substituent is $N(R_2)(R_3)$;

each $R_2$ and $R_3$ is, independently, H, $C_1-C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O; and $R_1$ is H or $C_1-C_{12}$ alkyl.

In further preferred embodiments of the compounds of the invention, oligonucleotide analogs are provided comprising at least one moiety having the Formula II:

Formula II

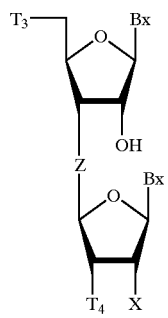

wherein:

each Z is a covalent intersugar linkage;

$T_3$ is a nucleotide other than a ribonucleotide, a nucleoside other than a ribonucleoside, hydroxyl, a blocked hydroxyl, or an oligonucleotide wherein the 3'-terminal nucleotide of said oligonucleotide is not a ribonucleotide.

$T_4$ is a nucleotide, a nucleoside, an oligonucleotide, a hydroxyl or a blocked hydroxyl;

with the proviso that at least one of said $T_3$ and $T_4$ is not a hydroxyl, or blocked hydroxyl;

$B_X$ is a heterocyclic base;

each X is, independently, F, —O—R, —S—R, or —N—R ($R_2$);

R is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;

and wherein any available hydrogen atom of said ring system is each replaceable with an alkoxy, alkylamino, urea or alkylurea group;

or R has one of the formulas:

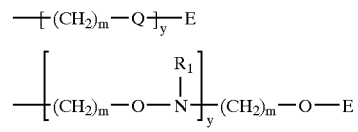

wherein

Q is O, S or $NR_2$;

m is from 1 to 10;

y is from 0 to 10;

E is $N(R_2)(R_3)$, $N=C(R_2)(R_3)$, $C_1-C_{10}$ alkyl, or $C_1-C_{10}$ substituted alkyl wherein said substituent is $N(R_2)(R_3)$; and each $R_2$ and $R_3$ is, independently, H, $C_1-C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O; and $R_1$ is H or $C_1-C_{12}$ alkyl.

In some preferred embodiments, compounds are provided that contain at least one moiety of Formula III:

III

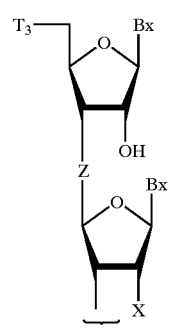

wherein:

Z is a covalent intersugar linkage;

$B_X$ is a heterocyclic base;

X is F, —O—R, —S—R or —$NR(R_2)$;

R is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;

and wherein any available hydrogen atom of said ring system is each replaceable with an alkoxy, alkylamino, urea or alkylurea group;

or R has one of the formulas:

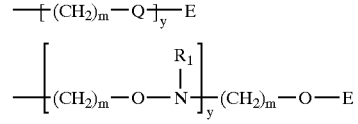

wherein

Q is O, S or $NR_2$;

m is from 1 to 10;

y is from 0 to 10;

E is $N(R_2)(R_3)$, $N=C(R_2)(R_3)$, $C_1-C_{10}$ alkyl, or $C_1-C_{10}$ substituted alkyl wherein said substituent is $N(R_2)(R_3)$;

each $R_2$ and $R_3$ is, independently, H, $C_1$–$C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O;

$T_3$ is a nucleotide other than a ribonucleotide, a nucleoside other than a ribonucleoside, a hydroxyl, a blocked hydroxyl, or an oligonucleotide wherein the 3'-terminal nucleotide of said oligonucleotide is not a ribonucleotide; and $R_1$ is H or $C_1$–$C_{12}$ alkyl.

In some preferred embodiments, oligonucleotide analogs of the invention are provided that contain a plurality of moieties of Formulas II or III.

In some preferred embodiments of the foregoing compounds, X is —O—R. In other preferred embodiments X is —O—R and R is —CH$_3$.

In further preferred embodiments of the compounds of the invention, R is —CH$_2$—CH$_2$—O—CH$_3$. In still further preferred embodiments of the compounds of the invention, Z is —N(CH$_3$)—O—CH$_2$—.

In preferred embodiments, oligonucleotide analogs of the invention are prepared to have a predetermined length. In some preferred embodiments, the length is from 1 to 200 subunits. In further preferred embodiments, the length is from 10 to 25 subunits, with from 12 to 20 subunits being more preferred.

DESCRIPTION OF PREFERRED EMBODIMENTS

The present invention provides modified nucleic acid dimeric compounds ("modified dimers"), and oligonucleotides and analogs thereof incorporating such modified dimers. The oligonucleotides and oligonucleotide analogs of the present invention can contain one modified dimer, or a plurality of modified dimers. Thus, the oligonucleotides and analogs of the invention can be essentially "nucleic acid like," (i.e., can contain primarily unmodified nucleic acid), or can contain modified dimers at several selected positions throughout the oligomer. The oligonucleotide analogs of the invention can have a plurality of modified dimers incorporated therein in any configuration.

In addition to having one or more modified dimers incorporated therein, oligonucleotide analogs of the present invention can be modified singly or uniformly at backbone, sugar and/or base positions.

Preferred modified dimers of the invention are illustrated by Formula I:

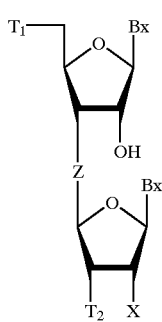

Formula I wherein:
each Z is a covalent intersugar linkage;
each $T_1$ and $T_2$ is, independently, —OH, —OR, —CH$_2$R, —NH(R), —SH, —SR, or a blocked hydroxyl;

$B_X$ is a heterocyclic base;
X is F, —O—R, —S—R or —NR($R_2$);
R is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;
and wherein any available hydrogen atom of said ring system is each replaceable with an alkoxy, alkylamino, urea or alkylurea group;
or R has one of the formulas:

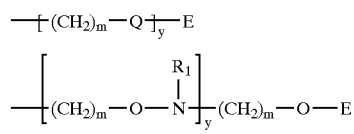

wherein
Q is O, S or NR$_2$;
m is from 1 to 10;
y is from 0 to 10;
E is N($R_2$) ($R_3$), N=C($R_2$) ($R_3$), $C_1$–$C_{10}$ alkyl, or $C_1$–$C_{10}$ substituted alkyl wherein said substituent is N($R_2$) ($R_3$)
each $R_2$ and $R_3$ is, independently, H, $C_1$–$C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O; and $R_1$ is H or $C_1$–$C_{12}$ alkyl.

In some preferred embodiments, oligonucleotides and oligonucleotide analogs of the present invention comprise at least one moiety having the Formula III:

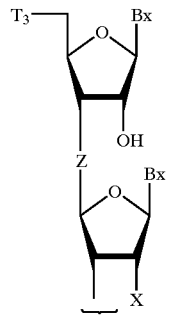

III wherein the constituent variables are as defined above.

In the modified dimers of the present invention, the covalently linked nucleosides are joined by a covalent intersugar (backbone) linkage which can be a naturally-occurring phosphodiester linkage, or a non-naturally occurring covalent intersugar (backbone) linkage. Preferred non-naturally occurring covalent intersugar (backbone) linkages are described below.

The nucleoside comprising the 5' end of the modified dimers of the invention comprise a ribose sugar, and the nucleoside comprising the 3' end of the modified dimers of the invention have a 2' modified ribosyl sugar moiety.

In some preferred embodiments, one or more modified dimers of the invention are incorporated into oligomers to form oligonucleotide analogs of the invention. Such oligonucleotide analogs are linear polymeric structures containing one or more modified dimers, and which can be attached to other monomeric or polymeric groups including additional modified dimers, nucleotides, nucleosides, oligonucleotides or oligonucleosides in any combination or order. Thus, oligonucleotide analogs of the invention are essentially covalently linked nucleosides joined by intersugar linkages, in which some of the adjacent nucleosides form modified dimers of the invention. In such embodiments, it is generally preferred that the nucleoside or nucleotide attached directly to the 5'-end of the modified dimer be a non-ribose nucleoside or nucleotide, such as, for example, a deoxyribonucleoside or deoxyribonucleoside.

In some preferred embodiments, oligonucleotide analogs of the invention contain one or more modified dimers which can be separated by one or more nucleotides or nucleosides. The modified dimer or modified dimers can be present in such oligonucleotide analogs at the terminal position (i.e., at the 3' or 5' end of the oligonucleotide analog), or at any number of non-terminal positions. Thus, in some preferred embodiments of the compounds of the invention, oligonucleotide analogs are provided comprising at least one moiety having the Formula II:

Formula II

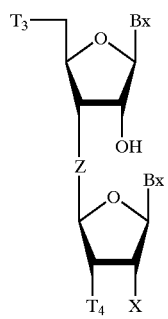

wherein:
each Z is a covalent intersugar linkage;
$T_3$ is a nucleotide other than a ribonucleotide, a nucleoside other than a ribonucleoside, a hydroxyl, a blocked hydroxyl, or an oligonucleotide wherein the 3'-terminal nucleotide of said oligonucleotide is not a ribonucleotide;
$T_4$ is a nucleotide, a nucleoside, an oligonucleotide, a hydroxyl or a blocked hydroxyl;
with the proviso that at least one of said $T_3$ and $T_4$ is not a hydroxyl, or blocked hydroxyl;
$B_x$ is a heterocyclic base;
each X is, independently, F, —O—R, —S—R, or —N—R ($R_2$);
R is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;
and wherein any available hydrogen atom of said ring system is each replaceable with an alkoxy, alkylamino, urea or alkylurea group;
or R has one of the formulas:

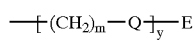

-continued

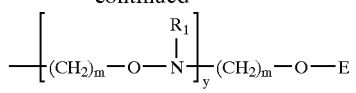

wherein
Q is O, S or $NR_2$;
m is from 1 to 10;
y is from 0 to 10;
E is $N(R_2)(R_3)$, $N=C(R_2)(R_3)$, $C_1$–$C_{10}$ alkyl, or $C_1$–$C_{10}$ substituted alkyl wherein said substituent is $N(R_2)(R_3)$; and
each $R_2$ and $R_3$ is, independently, H, $C_1$–$C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O; and $R_1$ is H or $C_1$–$C_{12}$ alkyl.

In one aspect of the present invention, the oligonucleotide analogs are from 1 to 200 linked nucleosides in length. A preferred length is from about 10 to about 25 linked nucleosides, with from about 12 to about 20 linked nucleosides being more preferred.

In the context of this invention, the term "oligonucleotide" refers to an oligomer or polymer of ribonucleic acid (RNA) or deoxyribonucleic acid (DNA). The term "oligonucleotide analog" refers to oligonucleotides composed of nucleobases, sugars and covalent intersugar (backbone) linkages that include portions that are non-naturally-occurring. Such modified or substituted oligonucleotides are often preferred over native forms because of desirable properties such as, for example, enhanced cellular uptake, enhanced affinity for nucleic acid target and increased stability in the presence of nucleases. A discussion of antisense oligonucleotides and some desirable modifications can be found, for example, in De Mesmaeker et al., *Acc. Chem. Res.*, 1995, 28, 366, incorporated herein by reference in its entirety.

As is known in the art, a nucleoside is a "base sugar combination." The base portion of the nucleoside is typically a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moieties of the sugar. In forming oligonucleotides, the phosphate groups covalently link adjacent nucleosides to one another to form a linear polymeric compound. In turn, the respective ends of this linear polymeric structure can be further joined to form, for example, a circular type structure. However, open linear structures are generally preferred.

The intersugar linkages are the groups that covalently join the sugar units of the oligonucleotide backbone. In naturally occurring oligonucleotides, the intersugar linkages are 3' to 5' phosphodiester linkages.

Examples of preferred oligonucleotides useful in the present invention include those containing modified backbones or non-natural intersugar linkages that connect the sugar units of the oligonucleotides. As used in this specification, oligonucleotides having modified backbones include both those that retain a phosphorous atom in the backbone, and those that do not have a phosphorous atom in the backbone. As used herein, the terms "oligonucleotide" and "modified oligonucleotide" are intended to include nucleosides that are connected by intersugar linkages that do not contain a phosphorous atom, and intersugar linkages that do contain a phosphorous atom.

In addition to phosphodiester intersugar linkages, other intersugar linkages are useful in the present invention. Thus, preferred modified oligonucleotide backbones useful in the present invention include, for example, phosphorothioates, chiral phosphorothioates, phosphorodithioates, phosphotriesters, aminoaklylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionphosphoramidates, thionalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. The various salts, mixed salts and free acids forms of the foregoing are also preferred.

Representative United States patents that teach the preparation of the above phosphorous atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred modified oligonucleotide backbones that do not include a phosphorous atom therein, i.e., oligonucleosides, have backbones that are formed by short chain alkyl or cycloalkyl intersugar linkages, mixed hetero atom and alkyl or cycloalky intersugar linkages or one or more or short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above "oligonucleosides" include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

More preferred embodiments include oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— of the above referenced U.S. Pat. No. 5,489,677, and the amide backbones of the above referenced U.S. Pat. No. 5,602,240. Also preferred are oligonucleotides having morpholino backbone structures of the above referenced U.S. Pat. No. 5,034,506.

Oligonucleotides may also include heterocyclic base (often referred to in the art as "nucleobase" or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia of Polymer Science And Engineering*, pages 858–859, Kroschwitz, J. I., ed. John Wiley & Sons, 1990, and those disclosed by Englisch et al., *Angewandte Chemie, International Edition*, 1991, 30, 613. Certain of these nucleobases are particularly useful for increasing the binding affinity of the oligonucleotide analogs of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton,1993, pp. 276–278) and are presently preferred base substitutions.

Representative United States patents that teach the preparation of certain of the above noted modified nucleobase as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned, and each of which is herein incorporated by reference, and commonly owned and allowed U.S. patent application Ser. No. 08/762,588, filed Dec. 10, 1996, also herein incorporated by reference.

Other preferred antisense compounds of the invention are formed as composite structures of at least one modified dimer and one or more oligonucleotides, modified oligonucleotides and or oligonucleosides as described above, or oligonucleotide mimetics. Such compounds have been referred to in the art as hybrids or "gapmers." Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and each of which is herein incorporated by reference, and commonly owned and allowed U.S. patent application Ser. No. 08/465,880, filed Jun. 6, 1995, also herein incorporated by reference.

Representative sugar modifications that are amenable to the present invention include 2' modifications such as OH, F, O—, S—, or N-alkyl, O—, S—, or N-alkenyl, or O, S— or N-alkynyl, wherein the alkyl, alkenyl and alkynyl are substituted or unsubstituted $C_1$ to $C_{10}$ alkyl or $C_2$ to $C_{10}$ alkenyl and alkynyl, particularly $O[(CH_2)_nO]_mOCH_3$, $O(CH_2)_nOCH_3$, $O(CH_2)_nNH_2$ or $O(CH_2)_nCH_3$ where n and m are from 1 to about 10. Other 2' modifications include $C_1$ to $C_{10}$ lower alkyl; substituted lower alkyl, alkaryl, araalkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy, i.e., an alkoxyalkoxy group (2'-O—$CH_2CH_2OCH_3$, also known as 2'-O—(2-methoxyethyl)) (Martin et al., *Helv. Chim. Acta*, 1995, 78, 486). Other preferred modifications include 2'-methoxy (2'-O—$CH_3$), 2'-aminopropoxy (2'-$OCH_2CH_2NH_2$) and 2'-fluoro (2'-F).

Further preferred sugar substituents include those disclosed in U.S. application entitled "RNA Targeted 2'-modified Oligonucleotides That Are Conformationally Preorganized" filed Jul. 27, 1998; U.S. Application entitled "Aminooxy-modified Oligonucleotides" filed Jan. 30, 1998; U.S. application entitled "Aminooxy-modified oligonucleotides And Methods For Making Same" filed Aug. 7, 1998; and U.S. application entitled "2'-o-dimethylaminoethyloxyethyl-modified Oligonucleotides", filed concurrently with the present application. Each of the foregoing applications is commonly owned by the assignee of the present application. The contents of each of the foregoing applications are hereby incorporated by reference in their entirety.

In further preferred embodiments of the present invention, oligonucleotides of the invention can be chemically linked to one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Let.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923), all references being incorporated herein by reference.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

Oligonucleotides of the invention may also be admixed, encapsulate, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764, incorporated herein by reference.

As used herein, the term "alkyl" includes but is not limited to straight chain and branch chain saturated hydrocarbon groups including but not limited to methyl, ethyl, and isopropyl groups. Alkyl groups of the present invention may be substituted. Representative alkyl substituents are disclosed in U.S. Pat. No. 5,212,295, at column 12, lines 41–50, hereby incorporated by reference in its entirety. The term cycloalkyl is intended to denote a cyclic alkyl group.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

In general, the term "hetero" denotes an atom other than carbon, preferably but not exclusively N, O, or S. Accordingly, the terms "heterocycloalkyl" and "heteroaryl" denote, respectively, a cycloalklyl or aryl moiety containing at least one heteroatom (i.e., non-carbon atom).

The term alkoxy denotes a group of formula —O-alkyl. The term "alkylamino" is intended to mean a group of formula —NH(R') or —N(R')(R") wherein R' and R" are each alkyl.

A number of chemical functional groups can be introduced into compounds of the invention in a blocked form and subsequently deblocked to form a final, desired compound. In general, a blocking group renders a chemical functionality of a molecule inert to specific reaction conditions and can later be removed from such functionality without substantially damaging the remainder of the molecule (Green and Wuts, Protective Groups in Organic Synthesis, 2d edition, John Wiley & Sons, New York, 1991). For example, amino groups can be blocked as phthalimido groups, as 9-fluorenylmethoxycarbonyl (FMOC) groups, and with triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX). Chemical functional groups can also be "blocked" by including them in a precursor form. Thus, an azido group can be used considered as a "blocked" form of an amine, because the azido group is easily converted to the amine.

In one embodiment oligonucleotide analogs of the invention are comprised of a plurality of modified dimers. When two or more modified dimers of the invention are present in an oligonucleotide analog of the invention, they may be located adjacent to one another, or they may be separated by one or more covalently linked nucleosidic subunits. In some preferred embodiments wherein three or more modified dimers are present in an oligonucleotide analog of the inventon, the modified dimers may be linked, (i.e., be adjacent to one another) separated by one or more nucleosidic subunits, or some may be linked and some may be separated. All such configurations are within the present invention.

The incorporation of 2'-hydroxyl groups on the 5'-nucleoside of modified dimers of the invention has been shown to stabilize the C-3 endo sugar pucker which is necessary for target RNA binding. A 2'-hydroxyl group is also able to form an intramolecular hydrogen bond with a sugar 0–4 ring atom on the 3' side which leads to intra strand axial stabilization. A 2'-hydroxyl group is also a recognition element in the interactions between proteins and RNA. 2'-Hydroxyl groups act as both donors and acceptors in a variety of intramolecular and intermolecular hydrogen bonding interactions that stabilize secondary structural motifs of RNA or RNA mimics providing a basis for polymorphic structure. 2'-Hydroxyl groups contribute to structure stabilization through bound water molecules and can function as ligands for coordinating metal cations which are involved in a wide variety of biological functions.

It has been surprisingly discovered that the oligonucleotide analogs of the present invention show enhanced affinity for complementary RNA. This enhanced affinity is illustrated in the examples below. Additional objects, advantages, and novel features of this invention will become apparent to those skilled in the art upon examination of the following examples thereof, which are intended to be illustrative and not intended to be limiting.

EXAMPLE 1

5-O-TIPS-1,2-O-isopropylidene-a-D-xylofuranose

A mixture of 1,2-O-isopropylidene-D-xylofuranose (Sigma Chemical Company) (8.96 g, 47 mmol) in dry DMF (100 mL), TIPSCl (10.0 g, 52 mmol), Et$_3$N (13 mL, 94 mmol) and DMAP (0.47 g, 3.9 mmol) was stirred overnight at rt then diluted with hexanes (500 mL) washed with water (4×100 mL), 0.05 N aqueous HCl (2×50 mL) water (100 mL), brine (100 mL) and dried over MgSO$_4$. The evaporated residue was purified on a short silica gel column with hexanes-EtOAc (12:1 and 4:1) to give 15.6 g (95%) of the title compound as a colorless oil.

$^1$H-NMR (CDCl$_3$,): d 1.03 (m, 21H, 3Pr$^1$), 1.27, 1.44 (2s, 6H, CMe$_2$), 4.06–4.24 (2m, 3H, H-4, H-5a, H-5b), 4.30 (d, 1H, H-3; J$_{3,4}$=2.6 Hz), 4.47 (d, 1H, H-2; J$_{1,2}$=3.7 Hz), 5.92(d, 1H, H-1), 4.36–4.52 (br, 1H, OH). $^{13}$C-NMR (CDCl$_3$,): d 11.57, 12.22 (3CH$\underline{Me}_2$), 17.60, 17.84, 17.88(3 $\underline{C}$HMe$_2$), 26.03, 26.69 (C$\underline{Me}_2$), 62.59(C-5), 76.76 (C-3), 78.29 (C-2), 85.44 (C-4), 104.85 (C-1), 111.31 ($\underline{C}$Me$_2$). CI MS (NH$_3$): 347 (MH$^+$); EI MS: m/z=331.19406 (M$^+$–15); C$_{16}$H$_{31}$O$_5$Si requires 331.19440.

EXAMPLE 2

3-Keto-5-O-TIPS-1,2-O-isopropylidene-a-D-xylose

5-O-TIPS-1,2-O-isopropylidene-a-D-xylose was oxidized following the procedure of Moffat using Ac$_2$O in DMSO. After workup and purification by vacuum distillation a 78% yield of the title compound was isolated.

The NMR spectra was consistent with the structure.

EXAMPLE 3

5-O-TIPS-3-deoxy-3-didehydro-3-[2-(1,3-dithianylidene)]-1,2-O-isopropylidene-a-D-ribofuranose To a solution of 2-(trimethylsilyl)-1,3-dithiane (prepared according to the procedure by Seebach, et al., *Chem. Ber*, 1973, 106, 2277) (384 mg, 2 mmol) in THF (4 mL) at −78° C. under argon was added dropwise 1.6 M BuLi in n-hexane (1.25 mL, 2 mmol). The mixture was allowed to warm to 0° C. in 3 hours and stirred at room temperature for 10 minutes and then cooled again to −78° C. 3-Keto-5-O-TIPS-1,2-O-isopropylidene-a-D-xylose (2 mmol, previously dried for overnight at rt over P$_2$O$_5$ under reduced pressure) in THF (4 mL) was added dropwise into the yellow solution of Li-dithiane. The mixture was gradually warmed to room temperature during an overnight stirring, then poured into water (30 mL) and extracted with CH$_2$Cl$_2$ (2×30 mL). The combined CH$_2$Cl$_2$ extracts were washed with water (5×10 mL), dried (MgSO$_4$) and evaporated to give 0.67 g of the crude title compound as a yellow oil. Purification was accomplished by elution over a silica gel column (2×30 cm) with EtOAc-hexanes (1:7) to give a 60% yield of the title compound as a colorless oil.

$^1$H-NMR (CDCl$_3$): d 1.03 (m, 21H, 3Pr$^1$), 1.41 (s, 6H, CMe$_2$), 2.12 (m, 2H, H-5'a,b), 2.76–3.06 (m, 4H, H-4'a,e, H-6'a,e), 3.76 (dd, 1H, H-5a; J$_{5a,5b}$=10.4, J$_{5a,4}$=1.9 Hz), 3.88 (dd, 1H, H-5b; J$_{5b,4}$=1.8 Hz), 4.91 (m, 1H, H-4'), 5.14 (dd, 1H, H-2; J$_{2,4}$=1.4, J$_{1,2}$=4.5 Hz), 5.97 (d, 1H, H-1). $^{13}$C-NMR (CDCl$_3$): d 11.86 (3C$\underline{H}$Me$_2$), 17.91 (3$\underline{C}$HMe$_2$), 24.10 (C-5'), 27.43, 27.77 (C$\underline{Me}_2$), 28.33, 28.77 (C-4', C-6'), 65.60 (C-5), 82.30, 82.84 (C-2, C-4), 105.81 (C-1), 112.54 ($\underline{C}$Me$_2$), 127.74 (C-3), 136.05 (C-2'). EI MS: m/z 446.20016(M$^+$); C$_{21}$H$_{38}$O$_4$S$_2$Si requires 446.20039.

EXAMPLE 4

3-Deoxy-3-didehydro-3-[2-(1,3-dithianylidene)]-1,2-O-isopropylidene-α-D-ribofuranose Into an ice-cold solution of 5-O-TIPS-3-deoxy-3-didehydro-3-[2-(1,3-dithianylidene)]-1,2-O-isopropylidene-α-D-ribofuranose (7.7 g, 17 mmol) in THF (150 mL) was quickly added 1M TBAF in THF (34 mL, 34 mmol). The mixture was left stirring in an ice bath for ½ hour and then the reaction quenched with water (10 mL) and concentrated. The residue was dissolved in EtOAc (750 mL), washed with water (8×100 mL) and brine (150 mL), dried (MgSO$_4$) and evaporated. The oily residue solidified after being kept in high vacuum overnight. Treatment with hexanes gave 4.2 g (85%) of the title compound in high purity (mp 101–4° C. (from hexanes-EtOAc).

$^1$H-NMR (CDCl$_3$): d 1.22, 1.25 (2s, 6H, CMe$_2$), 1.61 (apparent t, 1H, 5-OH), 1.97 (m, 2H, H-5'a,e), 2.64, 2.91 (2m, 4H, H-4'a,e, H-6'a,e), 3.51 (td, 1H, H-5a; J$_{5a,5b}$=11.7, J$_{5a,4}$=J$_{5a,5\text{-}OH}$=4.9 Hz), 3.60 (ddd, 1H, H-5b; J$_{5b,4}$=2.9, J$_{5b,5\text{-}OH}$=7.3 Hz), 4.74 (m, 1H, H-4), 5.02 (dd, 1H, H-2; J$_{1,2}$=4.4, J$_{2,4}$=1.9 Hz), 5.74 (d, 1H, H-1). $^{13}$C-NMR (CDCl$_3$): d 23.41 (C-5'), 27.13, 27.40 (C<u>Me</u>$_2$), 27.77, 28.19 (C-4', C-6') 62.83 (C-5), 81.14 (C-2), 82.78 (C-4), 104.51 (C-1), 111.33 (<u>C</u>Me$_2$), 127.77 (C-3), 135.16 (C-2'). EI MS: m/z 290.06500 (M$^+$); C$_{12}$H$_{18}$O$_4$S$_2$ requires 290.06464.

EXAMPLE 5

3-Deoxy-3-[2-(1,3-dithianyl)]-1,2-O-isopropylidene-a-D-ribofuranose

A solution of 3-deoxy-3-didehydro-3-[2-(1,3-dithianylidene)]-1,2-O-isopropylidene-α-D-ribofuranose (3.33 g, 11.5 mmol) in dry THF (40 mL) was added slowly into a well stirred suspension of LiAlH$_4$ (1.6 g, 43 mmol) in dry THF (100 mL) under argon. The mixture was stirred at 55° C. for 6 hours and then cooled in an ice bath. Successive dropwise additions of water (1.6 mL), 15% aqueous NaOH (1.6 mL) and water (4.8 mL) was followed by stirring at room temperature for 45 minutes. The mixture was filtered by suction and the filter cake washed with EtOAc (700 mL). The filtrate was evaporated and the residue partitioned between EtOAc (500 mL) and water (100 mL). The organic layer was washed with water (2×75 mL), saturated aqueous NaHCO$_3$ (75 mL), water (75 mL) and dried (MgSO$_4$). Evaporation of the solvent yielded 2.67 g (80%) of the title compound in high purity.

$^1$H-NMR (CDCl$_3$): d 1.33, 1.52 (2s, 6H, CMe$_2$), 1.91–2.01 (m, 2H, H-5'a, 5-OH), 2.01–2.09 (m, 1H, H-5'-e), 2.60–2.70 (m, 1H, H-3), 2.74–2.95 (3m, 4H, H-4'a,e, H-6'a,e), 3.92 (ddd, 1H, H-5a; J$_{5a,5b}$=12.2, J$_{5a,4}$=3.3, J$_{5a,5\text{-}OH}$=8.8 Hz), 4.01 (ddd, 1H, H-5b; J$_{5b,4}$=2.2, J5b,5-OH=4.7 Hz), 4.12 (td, 1H, H-4; J$_{4,3}$=9.8 Hz), 4.19 (d, 1H, H-2'; J$_{2',3}$=10.7 Hz), 4.81 (t, 1H, H-2; J1,2=J$_{2,3}$=3.9 Hz), 5.76 (d, 1H, H-1). $^{13}$C-NMR (CDCl$_3$): d 24.93 (C-5'), 26.01, 26.39 (C<u>Me</u>2), 27.73, 28.25 (C-4',C-6'), 41.75 (C-3), 62.51 (C-5), 80.64 (C-2), 81.44 (C-4), 103.23 (C-1), 111.64 (<u>C</u>Me$_2$). EI MS: m/z 292.08029(M$^+$); C$_{12}$H$_{21}$O$_4$S$_2$ requires 292.08050.

EXAMPLE 6

5-O-TBDPS-3-deoxy-3-[2-(1,3-dithianyl)]-1,2-O-isopropylidene-a-D-ribofuranose

To a solution of 3-deoxy-3-[2-(1,3-dithianyl)]-1,2-O-isopropylidene-a-D-ribofuranose (2.53 g, 8.7 mmol) in DMF (30 mL) and imidazole (1.18 g, 17.4 mmol) was added TBDPSCl (2.26 mL, 8.7 mmol). After stirring for 2 hours at room temperature the mixture was poured into water (1 L) and extracted with EtOAc (2×300 mL). The combined organic extracts were washed with water (5×150 mL), dried (MgSO$_4$) and evaporated to give 4.6 g (100%) of the title compound as a colorless oil which was used for acetolysis without any further purification.

$^1$H-NMR (CDCl$_3$): d 1.06 (s, 9H, Bu), 1.37, 1.52 (CMe$_2$), 2.01 (m, 2H, H-5'a,e), 2.69 (m, 1H, H-3), 2.80–3.06 (m, 4H, H-4'a,e, H-6'a,e), 4.05 (d, 2H, H-5a, H-5b; J$_{5a,4}$=J$_{5b,4}$=2.0 Hz), 4.14 (m, 2H, H-4, H-2'), 4.84 (apparent t, 1H, H-2), 5.80 (d, 1H, H-1; J$_{1,2}$=3.6 Hz), 7.34–7.40, 7.61–7.72 (2d, 10H, 2Ph). EI MS: m/z 473.13310 (M$^+$–57) C$_{24}$H$_{29}$O$_4$S$_2$Si requires 473.13332.

EXAMPLE 7

5-O-TBDPS-3-deoxy-3-[2-(1,3-dithianyl)]-1,2-di-O-acetyl-β-D-ribofuranose

To a solution of 5-O-TBDPS-3-deoxy-3-[2-(1,3-dithianyl)]-1,2-O-isopropylidene-a-D-ribofuranose (4.13 g, 7.8 mmol) in AcOH (119 mL) and Ac$_2$O (19 mL) at 75° C. was added CSA (5.45 g, 23.4 mmol) with stirring at 75° C. for 15 minutes. The mixture was cooled in an ice bath and poured into aqueous Na$_2$CO$_3$ (216 g in 1.38 L water). After stirring for ½ hour at room temperature the mixture was extracted with EtOAc (3×400 mL). The combined extracts were washed with saturated aqueous NaHCO$_3$ (3×200 mL) and water (300 mL), dried (MgSO$_4$) and evaporated to give a mixture of the title compound and the open chain 1-O-acetyl-1,2-β-isopropylidene sugar as a pale brown foam (4.4 g; 85% of the title compound was present in the mixture as determined from $^1$H-NMR). The mixture was separated on silica gel column (4.5×44 cm) with EtOAc-hexanes (1:12 and 1:6) to give 3.05 g (70%) of the title compound as a colorless foam.

The title compound: $^1$H-NMR (CDCl$_3$): d 1.06 (s, 9H, CMe$_3$), 1.76, 2.10 (2s, 6H, 2OAc), 1.95 and 2.15–2.30 (2m, 2H, H-5'a,e), 2.62–3.0 (m, 4H, H-4'a,e, H-6'a,e), 3.21 (dt, 1H, H-3; J$_{3,2}$=J$_{3,4}$=4.7, J$_{3,2'}$=9.7 Hz), 3.93 (dd, 1H, H-5a; J$_{5a,4}$=3.9, J$_{5a,5b}$=11.5 Hz), 4.03–4.12 (2m, 2H, H-2', H-5b), 4.32 (ddd, 1H, H-4; J$_{4,5}$b=1.7 Hz), 5.35 (d, 1H, H-2), 6.07 (s, 1H, H-1), 7.38, 7.69 (2m, 9H, 6H, 2Ph). $^{13}$C-NMR (CDCl$_3$): d 19.35 (<u>C</u>Me$_3$), 20.84, 20.95 (2CO<u>Me</u>), 25.45 (C-5'), 26.66, 26.86 (C<u>Me</u>$_3$), 28.76, 29.02 (C-4',C-6'), 42.54, 43.01 (C-3, C-2'), 65.34 (C-5), 77.53 (C-2), 84.79 (C-4), 98.10 (C-1), 127.64, 127.69, 129.59, 129.79, 135.45, 135.58 (3Ph), 169.42, 169.61 (2<u>C</u>OMe). EI MS: m/z 517.11747 (M+-57) C$_{25}$H$_{29}$O$_6$S$_2$Si requires 517.11700.

EXAMPLE 8

5-Methyl-2'-O-acetyl-5'-O-TBDPS-3'-deoxy-3'-[2-(1,3-dithianyl)]uridine

Prior to the preparation of the title compound a stock solution of bis(trimethylsilyl)thymine was prepared following the general procedure of Vorbrrueggen, et al., *Chem. Ber.* 1981, 114, 1234. A mixture of thymine (3.3 g, 30 mmol), HMDS (55 mL) and pyridine (22 mL) was stirred overnight at reflux and then distilled. At first the pressure of distillation was maintained at atmospheric and after all fractions had come over the distillation was continued at reduced pressure. The bis(trimethylsilyl)-thymine was collected at 0.21 Torr with a boiling point of 99–100° C. This material slowly solidified after being stored in a dessicator.

A solution of 5-O-TBDPS-3-deoxy-3-[2-(1,3-dithianyl)]-1,2-di-O-acetyl-β-D-ribofuranose (2.62 g, 4.6 mmol) in dry 1,2-dichloroethane (80 mL), bis(trimethylsilyl)thymine (1.36 mL, 5.0 mmol) and TMS-triflate (0.83 mL, 4.6 mmol) was stirred for ⅔ hour at reflux temperature under argon. The reaction mixture was cooled in an ice bath, poured into 5% aqueous NaHCO$_3$ (380 mL) and extracted three times with CH$_2$Cl$_2$ (400 mL, 2×150 mL). The combined extracts were washed with water (4×200 mL), dried (MgSO$_4$) and evaporated to give 3.0 g (100%) of the title compound as a pale yellow foam.

$^1$H-NMR (CDCl$_3$): d 1.10 (s, 9H, CMe$_3$), 1.49 (d, 3H, C5-Me, J$_{Me,H\text{-}6}$=0.9 Hz), 1.74–1.92 (m, 2H, H-2'Oa,e), 2.14

(s, 3H, COMe), 2.68–2.92 (m, 5H, H-3', H-4Óa,e, H-6Óa,e), 3.96 (dd, 1H, H-5'a; $J_{5'a,5'b}$=11.9, $J_{5'a,4}$=2.5 Hz), 4.14(d, 1H, H-2Ó; $J_{2\acute{6},3'}$=6.3 Hz), 4.18 (dd, 1H, H-5'b; $J_{5b,4}$=1.4 Hz), 4.38 (md, 1H, H-4', $J_{4',3'}$=7.8 Hz), 5.52 (dd, 1H, H-2'; $J_{2',1'}$=3.9, $J_{2',3'}$=7.3 Hz), 7.31–7.41, 7.63–7.71 (2m, 10H, 7H, 2Ph, H-6), 8.79 (s, 1H, NH). $^{13}$C-NMR (CDCl$_3$) d 11.85 (C5-Me), 19.45 (CMe$_3$), 20.95 (COMe), 25.37 (C-5Ó), 27.08 (CMe$_3$), 29.57, 30.18 (C-4Ó,C-6Ó), 43.85 (C-3'), 44.17 (C-2Ó), 64.53 (C-5'), 76.41 (C-2'), 81.99 (C-4'), 88.26 (C-1'), 111.39 (C-5), 127.83, 127.86, 129.90, 129.98, 132.56, 133.10, 8135.34, 135.57 (2Ph), 135.25 (C-6), 150.09 (C-4), 163.45 (C-2), 169.68(COMe). FAB MS: m/z 641(MH$^+$); EI MS m/z 583.13902(M$^{+\cdot}$57), C$_{28}$H$_{31}$N$_2$O$_6$S$_2$Si requires 583.13950.

EXAMPLE 9

5-Methyl-5'-O-tert-butyldiphenysilyl-3'-deoxy-3'-[2-(1,3-dithianyl)]uridine

To a mixture of 5-methyl-2'-O-acetyl-5'-O-TBDPS-3'-deoxy-3'-[2-(1,3-dithianyl)]uridine (3.2 g, 4.5 mmol) in MeOH (150 mL), was added dropwise aqueous 0.1 N aqueous NaOH (30 mL). After stirring overnight at room temperature 5 mL of 0.1 N aqueous NaOH was added and stirring continued for 8 hours. The mixture was neutralized by dropwise addition of 15% aqueous AcOH, diluted with MeOH (100 mL) and water (100 mL) and concentrated. The residue was partitioned between CH$_2$Cl$_2$ (750 mL) and water (400 mL). The aqueous layer was extracted with CH$_2$Cl$_2$ (2×200 mL) and the combined extracts washed with water (3×200 mL), dried (MgSO$_4$) and evaporated to give 2.54 g (95%) of the title compound in high purity as a pale yellow foam.

$^1$H-NMR (CDCl$_3$, 499.8 MHZ): d 1.12 (s, 9H, CMe$_3$), 1.35 (d, 3H, C5-Me; $J_{Me,H-6}$=0.7 Hz), 1.84–1.94 (m 1H, H-5 Óa) 2.03–2.11 (m, 1H, H-5Óe), 2.70 (dt, 1H, H-3'; $J_{3',2'}$=5.5, $J_{3',2\acute{6}}$=$J_{3',4}$=8.9 Hz), 2.83 (m, 2H, H-4Óa,e), 2.85, 2.91 (2m, 2H, H-6Óa,e), 4.14 (dd, 1H, H-5 'a; $J_{5'a,5'b}$=12.0, J5'a,4'=2.8 Hz), 4.32 (dd, 1H, H-5 'b; $J_{5'b,4}$=1.0 Hz), 4.44 (md, 1H, H-4'), 4.52 (dd, 1H, H-2'; $J_{2',3}$=5.4, $J_{1',2}$=1.5 Hz), 5.84 (d, 1H, H-1'), 7.38, 7.42, 7.68, 7.73 (4m, 10H, 2Ph), 7.64 (q, 1H, H-6). $^{13}$C NMR (CDCl$_3$) d 11.76 (C-5-Me), 19.56 (CMe$_3$), 25.50 (C-5Ó), 27.19 (2CMe$_3$), 30.16, 30.64 (C-4', C-6Ó), 44.41, 44.64 (C-2,Ó, C-3'), 64.43 (C-5'), 77.38 (C-2'), 83.24 (C-4'), 91.53 (C-1'), 110.65 (C-5), 127.72, 127.85, 129.90, 129.98, 132.76, 133.37, 135.29, 135.59 (2Ph), 135.10 (C-6), 150.69 (C-4), 163.91 (C-2). FAB MS: m/z 599(MH$^+$); EI MS m/z 541.12871 (M$^+$−57); C$_{26}$H$_{29}$N$_2$O$_5$S$_2$Si requires 541.12810.

EXAMPLE 10

5-Methyl-5'-O-TBDPS-3'-deoxy-3'-C-formyluridine

A mixture of 5-methyl-5'-O-tert-butyldiphenysilyl-3'-deoxy-3'-[2-(1,3-dithianyl)]uridine (2.44 g, 4.1 mmol) in degassed water-acetone (1:9, v/v; 200 mL), HgCl$_2$ (3.32 g, 12.3 mmol) and yellow HgO (2.65 g, 12.3 mmol) was vigorously stirred at reflux temperature for 12 hours. The reaction mixture was filtered through a celite pad which was thoroughly washed with CH$_2$Cl$_2$ (600 mL). The combined solutions were washed with 25% aqueous ammonium acetate (5×200 mL) and brine (300 mL), dried over Na$_2$SO$_4$ in an ice cold bath and evaporated to give 1.93 g (94%) of the title compound as a white solid (mp 132–8° C. (decomposition). This material was used directly for further coupling.

$^1$H NMR (CDCl$_3$) d 1.06 (s, 9H, CMe$_3$), 1.46 (d, 3H, C5-Me; $J_{Me,H-6}$=0.8 Hz), 1.9 (br, 1H, OH), 3.30 (dd, 1H, H-3'; $J_{3',4'}$=9.4, $J_{3',2'}$=5.7 Hz), 3.95 (dd, 1H, H-5'a; $J_{5'a,5'b}$=12.2, $J_{5'a,4'}$=2.4 Hz), 4.26 (dd, 1H, H-5'b; $J_{5'b,4'}$=1.8 Hz), 4.79 (apparent td, 1H, H-4'), 4.90 (d, 1H, H-2'), 5.75 (s, 1H, H-1'), 7.33–7.44 and 7.59–7.65 (2m, 6H, 4H, 2Ph), 7.67 (q, 1H, H-6), 9.83 (s, 1H, CHO), 10.24 (s, 1H, NH). $^{13}$C NMR (CDCl$_3$) d 12.00 (C5-Me), 19.45 (CMe$_3$), 27.03 (2CMe$_3$), 52.63 (C-3'), 63.11 (C-5'), 77.31 (C-2'), 80.90 (C-4'), 93.26 (C-1'), 110.75 (C-5), 127.95, 128.04, 130.07, 130.17, 132.26, 133.04, 135.18, 135.44 (2Ph,C-6), 150.84 (C-4), 164.43 (C-2), 197.81 (CHO) FAB MS: m/z 509 (MH$^+$); C$_{27}$H$_{33}$N$_2$O$_6$Si requires 509.20559.

EXAMPLE 11

3'-O-TBDPS-2'-O-methyl-5'-O-(N-methylamino)-5-methyluridine

To a solution of 3'-O-TBDPS-2'-O-methyl-5'-O-(methyleneimino)-5-methyluridine (prepared as per the procedure illustrated in Bhat et al., *J. Org. Chem.*, 1996, 61, 8186–8199) (8.02 g, 15.0 mmol) in acetic acid (75 mL) was cooled in an ice bath to 10° C. After 5 minutes at this temperature NaBH$_3$CN (1.0 g, 15.9 mmol) was added in one portion and the stirring continued at this temperature for 35 minutes. The bath was removed, the suspension allowed to warm to room temperature over 30 minutes. The reaction mixture was stirred at this temperature for an additional 30 minutes. It was then concentrated to a smaller volume (50 mL) under reduced pressure and poured into ice cold water (500 mL) and extracted in CH$_2$Cl$_2$ (3×120 mL), washed with water (2×50 mL) followed by aqueous NaHCO$_3$ solution (2×100 mL). The organic layer was then washed with brine (100 mL) and dried over anhydrous Na$_2$SO$_4$. The solvent was removed under reduced pressure and the product was purified by silica gel flash column chromatography using EtOAc:hexane (60/40, v/v) as the eluent. The appropriate fractions were combined and concentrated to give 7.0 g (87%) of the title compound.

R$_f$ 0.52 (EtOAc:hexane, 80/20, v/v). $^1$H NMR (CDCl$_3$) δ 8.48 (bs, 1H), 7.70–7.30 (m, 11H), 5.91 (d, J=2.5 Hz, 1H), 5.36 (bs, 1H), 4.23–4.06 (m, 2H), 3.98 (dd, 1H), 3.63 (dd, 1H), 3.35 (s, 3H), 3.22 (m, 1H), 2.63 (s, 3H), 1.83 (s, 3H), 1.10 s, (9H). HRMS (FAB$^+$, NBA/NaI) calcd for C$_{28}$H$_{37}$N$_3$O$_6$Si+Na$^+$562.2349, found 562.2336.

EXAMPLE 12

3'-De(oxyphosphinico)-3'-methylene(methylimino)-5'-O-TBDPS-5-methyluridinyl-(3>5)-3'-O-TBDPS-2'-O-methyl-5-methyluridine To an ice-cold solution of 5-methyl-5'-O-TBDPS-3'-deoxy-3'-C-formyluridine (1.36 g, 2.68 mmol) and 3'-O-TBDPS-2'-O-methyl-5'-O-(N-methylamino)-5-methyluridine (1.44 g, 2.68 mmol) in MeOH (12 mL) was added a solution of pyridinium para-toluene sulphonate (0.67 g, 2.67 mmol) in MeOH (2.5 mL) in one portion with stirring. Then pyridine-borage complex (325 mL, 2.67 mmol; M. in BH$_3$) was added dropwise and stirring was continued for 2.5 hours at room temperature. The mixture was partitioned between EtOAc (400 mL) and 5% aqueous NaHCO$_3$ (100 mL). The organic layer was washed with 5% aqueous NaHCO$_3$ (2×75 mL), brine (75 mL)and dried (MgSO$_4$). The organic layer was filtered and evaporated at reduced pressure. The resultant pale yellow foam (2.5 g) was applied to a silica gel column (4×38 cm), which was eluted first with MeOH—CH$_2$Cl$_2$ (1:50), then with MeOH—CH$_2$Cl$_2$ (1:30). Evaporation of the appropriate fractions yielded 1.45 g (52%) of the title MMI-dimer as a colorless foam in high purity.

$^1$H NMR ((CD$_3$)$_2$CO, 499.8 MHZ) (T1 and T2 represent 3'- and 5'-substituted ribo-thymidine moiety, respectively) d 1.08 (s, 18H, 2 CMe$_3$), 1.45 (d, 3H, T1:C5-Me; J$_{Me,H6}$=0.7 Hz), 1.74 (d, 3H, T2:C5-Me, J$_{MeH6}$=1.0 Hz), 2.52 (s, 3H, NMe), 2.54 (m, 1H, T1:H-3'), 2.80 (m, 1H, H-3Óa), 3.07 (dd, 1H, H-3Ób; J$_{3\acute{6}a,3\acute{6}b}$=11.3, J3',3Ób=8.2Hz), 3.21 (s, 3H, OMe), 3.49 (t, 1H, T2:H-2'; J$_{1',2'}$=4.1 Hz), 3.67 (dd, 1H, T2:H-5'a; J5'a,5'b=11.2, J$_{4',5'a}$=4.2 Hz), 3.84 (m, 1H, T2:H-5'b), 3.89 (dd, 1H, T1:H-5'a; J$_{5'a,5'b}$=11.7, J4',5'a=4.2 Hz), 4.10–4.19 (3m, 3H, T1:H-5'b,H-4', T2:H-4'), 4.23 (t, 1H, T2:H-3'; J$_{3',4'}$=J$_{2',4'}$=5.4 Hz), 4.46 (m, 1H, T1:H-2 '), 4.75 (d, 1H, 2'-OH; J$_{2',2}$"OH=2.7 Hz), 5.82 (d, 1H, T1:H-1'; J$_{1',2'}$=2.2 Hz), 5.93 (d, 1H, T2:H-1'; J$_{1',2'}$=3.7 Hz), 7.38–7.48, 7.66–7.69 and 7.71–7.77 (3m, 14H, 2H, 6H, 4Ph, 2H-6) 9.98 (s, 2H, 2NH). $^{13}$C NMR ((CD$_3$)$_2$CO, 50.31 MHZ) d 12.01, 12.40 (2C5-Me), 19.21, 19.42 (2CMe$_3$), 26.81, 27.03 (2C Me$_3$), 38.89 (NMe), 44.95 (T1:C-3'), 56.00 (T1:C-3Ó), 57.73 (OMe), 63.51 (T1:C-5'), 70.36 (T2:C-5',C-3'), 76.74 (T2:C-2'), 81.41 (T1:C-2'), 82.34, 83.38 (2C-4'), 88.77, 92.28 (2C-1'), 110.50, 110.56 (2C-5), 127.65, 127.79, 127.90, 127.94, 130.03, 130.08, 132.53, 132.77, 132.93, 133.01, 135.25, 135.42, 135.59, 135.73 (4Ph,2C-6), 149.92, 150.71 (2C-4), 163.87, 164.09 (2C-2). ES MS: m/z 1032.7 (M$^+$); C$_{55}$H$_{69}$N$_5$O$_{11}$Si$_2$ requires 1032.5.

EXAMPLE 13

3'-De(oxyphosphinico)-3'-methylene(methylimino)-5'-O-DMT-5-methyluridinyl-(3>5)-3'-O-TBDPS-2'-O-methyl-5-methyluridine A solution of 3'-de(oxyphosphinico)-3'-methylene (methylimino)-5'-O-TBDPS-5-methyluridinyl-(3>5)-3'-O-TBDPS-2'-O-methyl-5-methyluridine (0.765 g, 0.90 mmol), imidazole (0.100 g, 2.2 mmol) and TBDPSCl (0.317 g, 1.15 mmol) in anhydrous CH$_2$Cl$_2$ (10 mL) was stirred at room temperature for six hours. A sample of the reaction mixture analyzed by TLC (10% MeOH in CH$_2$Cl$_2$) indicated that the reaction was only 50% completed. An additional amount of imidazole (0.100 g 2.2 mmol) along with TBDPSCl (0.317 g, 0.90 mmol) was added and the stirring was continued for additional 2 hours. The reaction mixture was diluted with CH$_2$Cl$_2$ (50 mL) and washed with a saturated aqueous NaHCO$_3$ solution (2×20 mL), water (20 mL) and brine (20 mL). The organic layer was concentrated and purified by flash chromatography using a mixture of ethylacetate:hexane and methanol (60:35:5, v/v/v) as the eluant to give 0.917 g (93%) of the title compound as a colorless foam.

$^1$H NMR (DMSO-d$_6$) δ 11.34 and 11.34 (2S, 2H), 7.25–7.17 (m, 21H) 6.86–6.84 (m, 4H), 5.80 (d, 1H, J=2.2 Hz), 5.75 (d, 1H, J=2.4 Hz), 5.66 (bs, 1H) 4.21 (m, 1H), 4.06 (m, 2H), 3.97–3.96 (m, 1H), 3.69 (s, 6H), 3.52–3.51 (m, 1H), 3.49–3.37 (m, 3H), 3.32 (s, 3H), 3.12–3.07 (m, 4H), 2.80 (bs, 1H), 2.32 (s, 2H), 1.64 (s, 3H), 1.33 (s, 3H) and 0.99 (s, 9H). HRMS (FAB) for C$_{60}$H$_{69}$N$_5$O$_{13}$Si (MNa) 1118.4559, found 1118.4510.

EXAMPLE 14

3'-De(oxyphosphinico)-3'-methylene(methylimino)-5'-O-DMT-2'-O-acetyl-5-methyluridinyl (3>5)-3'-O-TBDPS-2'-O-methyl-5-methyluridine A solution of 3'-de(oxyphosphinico)-3'-methylene (methylimino)-5'-O-DMT-5-methyluridinyl-(3>5)-3'-O-TBDPS-2'-O-methyl-5-methyluridine (0.800 g, 0.74 mmole), acetic anhydride (0.098 g, 0.96 mmole), triethylamine(0.133 g, 1.3 mmole), and DMAP (0.025 g, 0.20 mmole) in anhydrous CH$_3$CN (10 mL) was stirred at room temperature for 2 hours. The TLC (10% MeOH in CH$_2$Cl$_2$) indicated the reaction was complete. The solvent was evaporated under reduced pressure and the residue was dissolved in EtOAc (50 mL), washed with aqueous saturated bicarbonate solution (2×10 mL) followed by water (10 mL). The organic layer was dried over anhydrous Na$_2$SO$_4$, solvent was removed to give a residue which was purified by column chromatography using ethylacetate:hexane:MeOH (60:35:5, v/v/v) as the eluent to give 0.72 g (85%) of the title compound as a colorless foam.

$^1$H NMR (CDCl$_3$) δ 8.26 and 8.24 (2s, 2H), 7.70–7.15 (m, 21H), 6.84–6.79 (m, 4H), 5.93 (d, 1H, J=3.6 Hz), 5.79 (d=2.3 Hz), 5.65–5.55 (m, 1H), 4.14–4.09 (m, 2H), 3.98–3.85 (m, 2H), 3.70 (bs, 7H), 3.60–3.50 (m, 3H), 3.25 (s, 3H), 3.24–3.05 (m, 2H), 2.85–2.70 (m, 2H), 2.37 (bs, 2H), 2.08 (s, 3H), 1.37 (s, 3H), 1.42 (s, 3H), 1.07 (s, 9H). HRMS (FAB) for C$_{62}$H$_{71}$N$_5$O$_{14}$Si (MNa) 1160.4664, found 1160.4702.

EXAMPLE 15

3'-De(oxyphosphinico)-3'-(methyleneimino)-5'-DMT-2'-O-acetyl-5-methyluridyl(3>5)-2'-O-methyl-5-methyluridine A mixture of compound 3'-de(oxyphinico)-3'-methylene(methylimino)-5'-O-DMT-2'-O-acetyl-5-methyluridinyl-(3>5)-3'-O-TBDPS-2'-O-methyl-5-methyluridine (0.70 g, 0.61 mmole) and TBAF on silica gel in anhydrous THF (10 mL) was stirred at room temperature for 15 hours. A sample of the mixture analyzed by TLC using ethyl acetate:hexane:MeOH (70:20:10, v/v/v) indicated the reaction had gone to completion. The mixture was directly loaded onto the silica gel column and eluted with the same solvent system. The appropriate fractions were concentrated to a foam that was triturated with ether. The resulting precipitate was removed by filtration and dried to give 0.45 g (82%) of the title compound as a colorless foam.

$^1$H NMR, (DMSO-d$_6$) δ 11.41 and 11.38 (2s, 2H), 7.59–7.26 (m, 15H), 6.91–6.86, (m, 4H), 5.83 (d, 1H, J=5.1 Hz), 5.79 (d, 1H, J=2.6 Hz), 5.85–5.43 (m, 1H), 5.25–5.20 (m, 1H), 4.18–3.80 (m, 3H), 3.74 (s, 6H), 3.34 (bs, 6H), 2.85–2.65, (m, 2H), 2.49 (bs, 2H), 2.09 (s, 3H), 1.73 (s, 3H), 1.53 (s, 3H). HRMS (FAB) for C$_{46}$H$_{53}$N$_5$O$_{14}$ (MNa+) 922.3487, found 922.3499.

EXAMPLE 16

3'-De(oxyphosphinico)-3'-(methyleneimino)-5'-DMT-2'-O-acetyl-5-methyluridylyl(3>5)-2'-O-methyl-5-methyluridine-3'-phosphoramidite A mixture of 3'-de(oxyphosphinico)-3'-(methyleneimino)-5'-DMT-2'-O-acetyl-5-methyluridylyl (3>5)-2'-O-methyl-5-methyluridine (0.417 g, 0.46 mmole), diisopropylaminotetrazolide (0.055 g, 0.31 mmole) and 2-cyanoethyl N,N,N',N' teraisopropylphosphoramidite (0.208 g, 0.69 mmole) in anhydrous CH$_3$CN (2.5 mL) was stirred at room temperature for 2 hours. TLC using acetone:CH$_2$Cl$_2$ (1:1, v/v) showed only 50% reaction was complete. An additional 0.69 mmole of the reagent was added and the reaction stirred for total of 20 hours. The reaction mixture was diluted with EtOAc (50 mL), washed with brine (2×10 mL), and dried over anhydrous Na$_2$SO$_4$.

The solvent was removed under reduced pressure to give a residual gum which was dissolved in $CH_2Cl_2$ (2 mL) and poured into a vigorously stirred solution of hexane (125 mL). The stirring was continued for about 10 minutes and the solid was collected by filtration and washed with hexane (2×10 mL). Drying gave 0.5 g and the colorless solid was dried under vacuum for 15 hours. Yield=0.500 g, 98% (90% purity by P-31 NMR, along with H-phosphonate of the reagent).

$^{31}P$ NMR ($CD_3CN$): δ 151.21 and 150.947 ppm HRMS (FAB) for $C_{55}H_{70}N_7O_{15}P$ (MNa+) 1122.4565, found 1122.4522.

EXAMPLE 17

2'-O-acetyl-3'-carboxymethyl-5'-O-DMT-5-methyluridine

5-Methyluridine is converted to the 5-O-DMT derivative and further acetylated using acetylbromide/DMAP. The 2'-O-acetyl-5-O-DMT-5-methyluridine is converted to the 3'-allyl derivative following a modification of Fiandor et al., *Tetrahedron Lett.*, 1990, 31, 597. Oxidation of the 3'-allyl derivative to the acid is accomplished using sodium chlorite.

EXAMPLE 18

5'-Amino-3'-tBuPh$_2$Si-2'-O-methyl-5-methyluridine

5-Methyluridine was converted to 5'-tosyl-3'-tBuPh$_2$Si-2'-O-methyl-5-methyluridine the title compound using methods described by DeMesmaeker, A., *Agnew. Chem. Intl. Ed. Engl.*, 1994, 33, 226. The tosylate is displaced by lithium azide and reduced to give the amine.

EXAMPLE 19

3'-De(oxyphosphinico)-3'-(methylcarboxyamino)-5'-DMT-2'-O-acetyl-5-methyluridylyl(3>5)-2'-O-methyl-5-methyluridine-3'-phosphoramidite The products of Examples 17 (acid) and 18 (amine) are condensed using HBTU in DMF. The lower sugar moiety is deprotected at the 3' position using F$^-$ in acid and phosphitylated to give the title modified dimer. The modified dimer is utilized further in the standard oligomer synthesis scheme illustrated in Example 30.

EXAMPLE 20

2'-O-(chloroethoxyethyl)-3'-amino-5-methyl-5'-O-DMT-uridine 5-methyl-uridine is converted to 2'-O-(chloroethoxyethyl)-5-methyl uridine according to the procedure of Yamakage described in *Tetrahedron Lett*, 1989, 30, 6361–6364. This material is converted to 3'-anhydro derivative by treating with diphenyl carbonate in DMF according to the procedure described in "Nucleic Acids in Chemistry and Biology," G. M. Blackburn and M. J. Gait, Oxford University Press 1996 p. 90. This 3'-anhydro compound is treated with LiN$_3$/DMF to give 2'-O-chloroethoxyethyl-3'-azido-5-methyl-uridine which on treatment with DMT-Cl/pyridine gave the corresponding 5'-dimethoxytrityl derivative. This compound was reduced using dithiothreitol in 0.1 M phosphate buffer/DMF according to the modification of a procedure suggested by Handlon and Oppenheimer described in *Pharmaceutical Research*, 1988, 5, 297, to give the title compound.

EXAMPLE 21

2'-O-methyl-31-amino-5-methyl-5'-O-DMT-uridine

The procedure illustrated in Example 20 is repeated with 2'-O-methyl-5-methyl-uridine (Chemgenes, Waltham, Mass.) as the starting material. In this case, 2'-protection with a chloroethoxyethyl group is not required to obtain the title compound.

EXAMPLE 22

Oligomer Synthesis

Solid support bound 2'-O-methyl-5-methyl-5'-O-DMT-uridine attached to solid support through the 3'-O— is purchased from ChemGenes. The 5'-O-DMT blocking group is removed as per standard protocols. The 5'-hydroxyl group is phosphitylated to the 5'-H-phosphonate-2-cyanoethyl diester. The solid support bound material is coupled via oxidative phosphorylation to the product of Example 20 to give a modified dimer in a protected form. The modified dimer can be elongated by addition of nucleosides and or nucleotides. Additional modified dimers are added by coupling the product of Example 21 followed by the coupling of the product of Example 20. The chloroethoxyethyl group is removed during the oligonucleotide deprotection step by adjusting the pH to ca. 2.0.

EXAMPLE 23

2'-O-TBDPS-3'-carbony-5-methyl-5'-O-DMT-uridine

The title compound is prepared as adapted from the procedure of Xie et al., *Tetrahedron Lett.*, 1996, 37, 4443–4446.

EXAMPLE 24

2'-O-methyl-3'-carbony-5-methyl-5'-O-DMT-uridine

The title compound is prepared as adapted from the procedure of Samano et al., *Synthesis*, 1991, 4, 282–288.

EXAMPLE 25

2'-O-TBDPS-3'-methylene-5-methyl-5'-O-DMT-uridine

The title compound is prepared from the product of Example 23 according to the procedure of Samano ibid.

EXAMPLE 26

2'-O-methyl-31-methylene-5-methyl-5'-O-DMT-uridine

The title compound is prepared from the product of Example 24 according to the procedure of Samano ibid.

EXAMPLE 27

2'-O-TBDPS-3'-(H-phosphonylmethyl)-5-methyl-5'-O-DMT-uridine

The title compound is prepared from the product of Example 25 according to the procedure of Nifantev et al., *Chem. Abst.*, 1956, 50, 10124d.

EXAMPLE 28

2'-O-methyl-3'-(H-phosphonylmethyl)-5-methyl-5'-O-DMT-uridine

The title compound is prepared from the product of Example 26 according to the procedure of Nifantev et al., *Chem. Abst.*, 1956, 50, 10124d.

EXAMPLES 29–56
Procedures for the preparation of compounds of the formula:

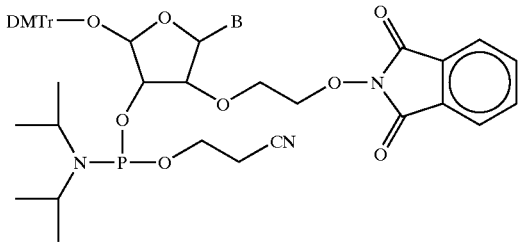

wherein:

B is a heterocyclic base moiety and DMTr is dimethoxytrityl.

EXAMPLE 29

Methyl-2-O-(2-ethylacetyl)-3,5-bis-O-(2,4-dichlorobenzyl)-α-D-ribofuranoside

1-O-Methyl-3,5-bis-O-(2,4-dichlorobenzyl)-α-D-ribofuranoside (prepared from 1-O-methyl-2,3,5-tris-O-(2,4-dichlorobenzyl)-α-D-ribofuranoside via the literature procedure, Martin, P. *Helv. Chem. Acta*, 1995, 78, 486–504) was dissolved in DMF (86 mL) with cooling to 5° C., and NaH (60% dispersion, 1.38 g, 34.38 mmol) was added. The reaction mixture was stirred at 5° C. for 5 minutes then warmed to ambient temperature and stirred for 20 minutes after which time the reaction mixture was cooled to 5° C. and ethylbromoacetate (3.81 mL, 34.4 mmol) was added dropwise resulting in the evolution of gas. The reaction mixture was allowed to warm to ambient temperature and stirred for 3 hours after which time the mixture was cooled to 5° C. and the pH was adjusted to 3 with saturated aqueous $NH_4Cl$. The solvent was evaporated in vacuo to give a syrup which was dissolved in EtOAc (200 mL), washed with water and then brine. The organic layer was separated, dried with $MgSO_4$, and the solvent was evaporated in vacuo to give an oil. The oil was purified by flash chromatography using hexanes-EtOAc, 60:40, to give the title compound as an oil (15.52 g, $^1$H NMR ($CDCl_3$): δ 7.58–7.18 (m, 6H), 5.05 (d, J=3.8 Hz, 1H), 4.79 (q, $J_{AB}$=13.7 Hz, 2H), 4.57 (d, J=2.8 Hz, 2H), 4.31–4.16 (m, 5H), 4.03 (m, 2H), 3.62 (d, 2H), 3.50 (s, 3H), 1.28 (t, 3H). $^{13}$C NMR ($CDCl_3$): δ 170.0, 134.2, 133.6, 133.5, 130.3, 129.8, 129.1, 128.8, 127.1, 102.1, 81.4, 78.9, 76.6, 70.6, 70.0, 69.3, 67.6, 61.0, 55.6, 14.2. Anal. Calcd for $C_{24}H_{26}Cl_4O_7.H_2O$: C, 49.17; H, 4.81. Found: C, 49.33; H, 4.31.

EXAMPLE 30

1-[2'-O-(2-ethylacetyl)-3',5'-bis-O-(2,4-dichlorobenzyl)-β-D-ribofuranosyl]thymine Thymine (6.90 g, 54.6 mmol) was suspended in anhydrous dichloroethane (136 mL) and bis-trimethylsilylacetamide (40.5 mL, 164 mmol) was added. The reaction mixture was heated to reflux temperature for 10 minutes to give dissolution. After cooling to ambient temperature, the solution was added to compound methyl-2-O-(2-ethylacetyl)-3,5-bis-O-(2,4-dichlorobenzyl)-α-D-ribofuranoside with stirring. Trimethylsilyl trifluoromethanesulfonate (6.86 mL, 35.5 mmol) was added and the reaction mixture was heated to reflux for 6 hours. The mixture was cooled to 5° C. and the pH was adjusted to 7 by the slow addition of saturated $NaHCO_3$. The mixture was extracted with $CH_2Cl_2$ (3×150 mL) and the organic extracts were combined, washed with brine, and the solvent was evaporated in vacuo to give an oil. The oil was dissolved in $CH_2Cl_2$ and purified by flash chromatography using hexanes-EtOAc, 45:55, to provide the title compound as an oil (7.92 g, 44%). (The α-anomer was contained in a later fraction).

$^1$H NMR (400 MHZ, $CDCl_3$): δ 8.25 (s, 1H), 7.67 (s, 1H), 7.46–7.21 (m, 6H), 5.94 (d, J=1.6 Hz, 1H), 4.80 (q, $J_{AB}$=12.4 Hz, 2H), 4.70–4.18 (m, 9H), 4.02 (d, 1H), 3.75 (d, 1H), 1.58 (s, 3H), 1.26 (t, 3H). $^{13}$C NMR ($CDCl_3$): δ 170.1, 164.3, 150.3, 135.5, 134.5, 134.2, 134.1, 133.8, 133.5, 130.7, 130.2, 129.4, 129.0, 127.1, 110.3, 88.4, 80.8, 80.5, 74.7, 70.1, 68.9, 68.0, 66.2, 60.9, 14.1, 12.1. Anal. Calcd for $C_{28}H_{28}Cl_4N_2O_8.H_2O$: C, 49.43; H, 4.44; N, 4.12. Found: C, 49.25; H, 4.10; N, 3.94.

EXAMPLE 31

1-[2'-O-(2-hydroxyethyl)-3',5'-bis-O-(2,4-dichlorobenzyl)-β-D-ribofuranosyl]thymine 1-[2'-O-(2-Ethylacetyl)-3',5'-bis-O-(2,4-dichlorobenzyl)-β-D-ribofuranosyl]thymine (9.92 g, 15.0 mmol) was dissolved in hot EtOH (150 mL) and the solution was cooled to ambient temperature in a water bath. To the solution was cautiously added $NaBH_4$ (1.13 g, 30.0 mmol) over 10 minutes. After 3 hours additional $NaBH_4$ (282 mg, 7.45 mmol) was added the mixture was stirred for 1 hour and left to stand for 8 hours. The pH was adjusted to 4 by addition of Saturated $NH_4Cl$ (25 mL) to give a gum. The solvent was decanted and evaporated in vacuo to afford a white solid which was dissolved in $CH_2Cl_2$ (250 mL). The gum was dissolved with saturated aqueous $NaHCO_3$ and this solution was gently extracted with the $CH_2Cl_2$ containing the product. The organic layer was separated and the aqueous layer was extracted again with $CH_2Cl_2$ (2×50 mL). After combining the organic layers, the solvent was dried over $MgSO_4$ and evaporated in vacuo to afford a white foam. The foam was dissolved in $CH_2Cl_2$ and purified by flash chromatography using hexanes-EtOAc, 20:80, to give the title compound as a white foam (8.39 g, 90%).

$^1$H NMR ($CDCl_3$): δ 10.18 (s, 1H), 7.66 (s, 1H), 7.39–7.20 (m, 6H), 5.96 (s, 1H), 4.76–3.62 (m, 14H), 1.58 (s, 3H). $^{13}$C NMR ($CDCl_3$): δ 164.0, 150.8, 135.2, 134.6, 134.2, 134.1, 133.5, 133.4, 130.2, 129.4, 129.0, 127.1, 110.6, 88.6, 81.0, 80.7, 75.2, 72.0, 70.1, 68.9, 68.1, 61.9, 12.1.

EXAMPLE 32

1-[2'-O-(2-phthalimido-N-hydroxyethyl)-3',5'-bis-O-(2,4-dichlorobenzyl)-β-D-ribofuranosyl]thymine 1-[2'-O-(2-Hydroxyethyl)-3',5'-bis-O-(2,4-dichlorobenzyl)-β-D-ribofuranosyl]thymine was dried by coevaporation with anhydrous acetonitrile followed by further drying in vacuo (0.1 torr) at ambient temperature for 12 h. The dried material (8.39 g, 13.53 mmol) was dissolved in freshly distilled THF (97 mL), $PPh_3$ (3.90 g, 14.9 mmol), and N-hydroxyphthalimide (2.43 g, 14.9 mmol) was added. The reaction mixture was cooled to −78° C., and diethyl azodicarboxylate (2.34 mL, 14.9 mmol) was added. The reaction mixture was warmed to ambient temperature and the solvent was evaporated in vacuo to give a foam. The foam was dissolved in EtOAc (100 mL) and washed with saturated aqueous $NaHCO_3$ (3×30 mL). The organic layer was separated, washed with brine, dried over $MgSO_4$, and the solvent evaporated to give a foam. The foam was purified by flash chromatography using $CH_2Cl_2$-acetone, 85:15, to give the title compound as a white foam (3.22 g, 31%). A second chromatographic purification provided additional title compound as a white foam (5.18 g, 50%).

$^1$H NMR (400 MHZ, $CDCl_3$): δ 9.0 (s, 1H), 7.8 (m, 11H), 5.95 (s, 1H), 4.84–3.70 (m, 13H), 1.60 (s, 3H). $^{13}$C NMR (100 MHZ, $CDCl_3$): δ 163.7, 163.5, 150.2, 138.0, 135.6, 134.5, 134.1, 134.0, 133.9, 133.7, 133.6, 130.6. 130.4, 130.1, 129.8, 129.4, 129.1, 129.0, 128.8, 127.2, 123.5, 110.4, 88.2, 81.0, 80.9, 77.6, 75.4, 70.2, 68.9, 68.4, 68.1, 12.1. LRMS (FAB+) m/z: 766 (M+H). LRMS (FAB–) m/z: 764 (M–H).

EXAMPLE 33

1-[2'-O-(2-phthalimido-N-oxyethyl)-3',5'-bis-O-(2,4-dichlorobenzyl)-β-D-ribofuranosyl]thymine 1-[2'-O-(2-phthalimido-N-hydroxyethyl)-3',5'-bis-O-(2,4-dichlorobenzyl)-β-D-ribofuranosyl]thymine (1.79 g, 2.34 mmol) was dissolved in $CH_2Cl_2$ (12 mL), the solution was cooled to −78° C. and 1.0 M boron trichloride (5.15 mL, 5.15 mmol) in $CH_2Cl_2$ was added and the reaction mixture was kept at 5° C. for 1.5 hours. Additional 1.0 M boron trichloride (5.15 mL, 5.15 mmol) in $CH_2Cl_2$ was added and the solution was stirred at 5° for an additional 1.5 hours. The pH was adjusted to 7 with saturated aqueous $NaHCO_3$ (30 mL). After dilution with $CH_2Cl_2$ (100 mL), the organic layer was separated, and the aqueous layer was extracted with $CHCl_3$ (5×25 mL) and then EtOAc (3×25 mL). The organic layers were combined, dried over $Na_2SO_4$, and evaporated in vacuo to give an oil. The oil was purified by flash chromatography using $CH_2Cl_2$-acetone, 45:55, to provide the title compound as a white foam (619 mg, 59%).

$^1$H NMR ($CDCl_3$): δ 8.8 (br, 1H), 7.88–7.75 (m, 4H), 7.50 (s, 1H), 5.70 (d, J=4 Hz, 1H), 4.45–3.75 (m, 11H), 2.95 (br, 1H), 1.90 (s, 3H). $^{13}$C NMR (100 MHZ, $CDCl_3$): δ 164.3, 163.7, 150.6, 137.4, 134.7, 128.5, 123.6, 110.5, 89.7, 84.7, 81.9, 77.6, 68.5, 68.4, 61.0, 12.3. LRMS (FAB+) m/z: 448 (M+H). LRMS (FAB–) m/z: 446 (M–H).

EXAMPLE 34

1-[2'-O-(2-phthalimido-N-oxyethyl)-5'-O-(4,4'-dimethoxytrityl)-β-D-ribofuranosyl]thymine 1-[2'-O-(2-phthalimido-N-oxyethyl)-3',5'-bis-O-(2,4-dichlorobenzyl)-β-D-ribofuranosyl]thymine was dried by coevaporation with anhydrous acetonitrile followed by further drying in vacuo (0.1 torr) at ambient temperature for 12 hours. The dried material (619 mg, 1.38 mmol) was dissolved in anhydrous pyridine (7 mL) and 4,4'-dimethoxytrityl chloride (514 mg, 1.52 mmol) was added. After 2 hours additional 4,4'-dimethoxytrityl chloride (257 mg-0.76 mmol) was added. The solution was stirred for 2 hours and a final addition of 4,4'-dimethoxytrityl chloride (257 mg, 0.76 mmol) was made. After 12 h MeOH (10 mL) was added to the reaction mixture, it was stirred for 10 min and the solvent was evaporated in vacuo to give an oil which was coevaporated with toluene. The oil was purified by flash chromatography by pre-treating the silica with $CH_2Cl_2$-acetone-pyridine, 80:20:1, then using $CH_2Cl_2$-acetone, 80:20 to afford the title compound as a yellow solid (704 mg, 68%).

$^1$H NMR ($CDCl_3$): δ 7.8–6.8 (m, 18H), 5.94 (d, J=2.2 Hz, 1H), 4.57–4.12 (m, 7H), 3.78 (s, 6H), 3.53 (m, 2H), 1.34 (s, 3H). $^{13}$C NMR ($CDCl_3$): δ 164.3, 163.8, 158.6, 150.6, 144.4, 135.5, 135.4, 134.7, 130.1, 128.7, 128.2, 128.0, 127.1, 123.7, 113.3, 110.9, 87.9, 86.7, 83.2, 68.7, 68.5, 61.7, 55.2, 11.9. LRMS (FAB+) m/z: 750 (M+H). LRMS (FAB–) m/z: 748 (M–H). Anal. Calcd for $C_{41}H_{39}N_3O_{11}.H_2O$: C, 65.14; H, 5.38; N, 5.47. Found: C, 63.85; H, 5.16; N, 5.14. Anal. Calcd for $C_{41}H_{39}N_3O_{11}$: C, 65.68; H, 5.24; N, 5.60. Found: C, 65.23; H, 5.27; N, 5.45.

EXAMPLE 35

1-[2'-O-(2-phthalimido-N-oxyethyl)-5'-O-(4,4'-dimethoxytrityl)-β-D-ribofuranosyl]thymine-3'-[(2-cyanoethyl)-N,N-diisopropylphosphoramidite]

1-[21-O-(2-phthalimido-N-oxyethyl)-5'-O-(4,4'-dimethoxytrityl)-β-D-ribofuranosyl]thymine was dried by coevaporation with anhydrous pyridine (2×20 mL), then further dried in vacuo (0.1 torr) at ambient temperature for 12 hours. The dried material (704 mg, 0.939 mmol) was dissolved in $CH_2Cl_2$ (9 mL), diisopropylamine tetrazolide (80.4 mg, 0.47 mmol) and 2-cyanoethyl-N,N,N$^1$,N'-tetraisopropylphosphorodiamidite (0.33 mL, 1.03 mmol) with stirring. After 2 hours at ambient temperature additional 2-cyanoethyl-N,N,N',N'-tetraisopropylphosphorodiamidite (0.33 mL, 1.03 mmol) was added and the solution was stirred for 20 hours. The solvent was evaporated in vacuo to give an oil which was purified by flash chromatography by pre-treating the silica with $CH_2Cl_2$-acetone-pyridine, 85:15:1, then using $CH_2Cl_2$-acetone, 85:15 to afford the title compound as an oil (704 mg, 68%). The product was coevaporated with anhydrous acetonitrile (2×30 mL) and $CH_2Cl_2$ (2×30 mL) to afford a yellow foam.

$^1$H NMR ($CDCl_3$): δ 8.6 (br, 1H), 7.78–6.82 (m, 18H), 6.06 (m, 1H), 4.6–3.3 (m, 14H), 3.75 (s, 6H), 2.66 (m, 1H), 2.37 (m, 1H), 1.36 (s, 3H), 1.16 (m, 12H). $^{31}$P NMR ($CDCl_3$): δ 150.5, 151.2. LRMS (FAB+) m/z: 950 (M+H). LRMS (FAB–) m/z: 948 (M–H). Anal. Calcd for $C_{50}H_{56}N_5O_{12}P.H_2O$: C, 62.04; H, 6.04; N, 7.24. Found: C, 62.20; H, 5.94; N, 7.34.

EXAMPLE 36

2'-O-(2-ethylacetyl)-3',51-O-(1,1,3,3-tetraisopropyldisiloxane-1,3-diyl)adenosine Adenosine (30.00 g, 112 mmol) was dissolved in hot anhydrous DMF (600 mL) and the solution was cooled to ambient temperature. NaH (60% dispersion oil, 4.94 g, 124 mmol) was added and the mixture was stirred with a mechanical stirrer for 1 hour. The resulting suspension was cooled to 5° C. and ethylbromoacetate (13.7 mL, 124 mmol) was added. The resulting solution was stirred for 12 hours at ambient temperature and the solvent was evaporated in vacuo to give a residue which contained 2'-O-(2-ethylacetyl) adenosine and the putative 3'-O-isomer. This material was coevaporated with pyridine to give a foam which was dissolved in anhydrous pyridine (400 mL). 1,3-Dichloro-1, 1,3,3-tetraisopropyldisiloxane (39.52 mL, 124 mmol) was added and the solution was stirred for 24 hours at ambient temperature. The solvent was evaporated in vacuo to give an oil which was dissolved in EtOAc (500 mL) and washed with brine three times. The organic layer was separated, dried over $MgSO_4$, and the solvent was evaporated in vacuo to afford an oil. The oil was purified by flash chromatography using hexanes-EtOAc, 80:20, to give the title compound as an oil (14.63 g, 22%).

$^1$H NMR (CDCl$_3$): δ 8.26 (s, 1H), 8.07 (s, 1H), 6.20 (br s, 2H), 4.91 (dd, J$_{1',2'}$=4.7 Hz, J$_{2',3'}$=9.3 Hz, 1H), 4.64–3.97 (m, 8H), 1.22 (t, 3H), 1.05 (m, 28H). $^{13}$C NMR (CDCl$_3$): δ 170.0, 155.5, 152.8, 149.0 139.3, 120.2, 88.6, 82.2, 81.1, 69.9, 68.3, 60.8, 60.0, 17.2, 14.0, 12.7. Anal. Calcd for C$_{26}$H$_{45}$N$_5$O$_7$Si$_2$: C, 52.41; H, 7.61; N, 11.75, Si, 9.43. Found: C, 52.23; H, 7.34; N, 11.69.

EXAMPLE 37

2'-O-(2-hydroxyethyl)-3',5'-O-(1,1,3,3-tetraisopropyldisiloxane-1,3-diyl)adenosine 2'-O-(2-ethylacetyl)-3',5'-O-(1,1,3,3-tetraisopropyldisiloxane-1,3-diyl)adenosine (4.175 g, 7.01 mmol) was dissolved in ethanol (95%, 40 mL) and the resulting solution was cooled to 5° C. NaBH$_4$ (60% oil dispersion, 0.64 g, 16.8 mmol) was added, and the mixture was allowed to warm to ambient temperature. After stirring for 12 hours CH$_2$Cl$_2$ (200 mL) was added and the solution was washed with brine twice and the organic layer was separated. The organic layer was dried over MgSO$_4$, and the solvent was evaporated in vacuo to give an oil. The oil was purified by flash chromatography using EtOAc-MeOH, 95:5, to afford the title compound as an oil (0.368 g, 9.5%).

$^1$H NMR (CDCl$_3$): δ 8.31 (s, 1H), 8.14 (s, 1H), 6.18 (br S, 2H), 6.07 (s, 1H), 4.62 (dd, J$_{1',2'}$=4.6 Hz, J$_{2',3'}$=9.4 Hz, 1H), 4.3–3.5 (m, 8H), 1.03 (m, 28H). $^{13}$C NMR (CDCl$_3$): δ 155.5, 153.0, 148.7, 138.3, 120.3, 89.2, 82.7, 81.4, 73.5, 69.3, 61.8, 59.7, 17.2, 17.0, 16.8, 13.4, 12.9, 12.8, 12.6.

LRMS (FAB+) m/z: 554 (M+H), 686 (M+Cs+).

EXAMPLE 38

2'-O-(2-Phthalimido-N-hydroxyethyl)-3',5'-O-(1,1,3,3-tetraisopropyldisiloxane-1,3-diyl)adenosine To a solution of 2'-O-(2-hydroxyethyl)-3',5'-O-(1,1,3,3-tetraisopropyldisiloxane-1,3-diyl)adenosine (0.330 g, 0.596 mmol) in anhydrous THF (10 mL) was added triphenylphosphine (0.180 g, 0.685 mmol) and N-hydroxyphthalimide (0.112 g, 0.685 mmol). To this mixture diethyl azodicarboxylate (0.11 mL, 685 mmol) was added dropwise at 5° C. After stirring for 3 hours at ambient temperature, the solvent was evaporated to give an oil. The oil was dissolved in EtOAc and washed with saturated aqueous NaHCO$_3$ (×3) and brine. The organic layer was separated, dried over MgSO$_4$. The solvent was evaporated in vacuo to give an oil. The oil was purified by flash chromatography using EtOAc-MeOH, 95:5, to give the title compound as an oil (0.285 g, 68%).

$^1$H NMR (CDCl$_3$): δ 8.21 (s, 1H), 8.05 (s, 1H), 7.8–7.45 (m, 4H), 6.00 (s, 1H), 5.88 (br s, 2H), 4.92 (dd, J$_{1',2'}$=4.6, J$_{2',3'}$=9.0 Hz), 4.5–3.9 (m, 8H), 1.0 (m, 28H). $^{13}$C NMR (CDCl$_3$): δ 163, 155.3, 152.8, 149, 139.6, 134.3, 123.4, 120, 88.7, 82.7, 81.1, 77.4, 70.2, 69.5, 60.1, 17.4, 17.2, 17.0, 16.9, 13.3, 12.9, 12.7, 12.6. LRMS (FAB+) m/z: 699 (M+H).

EXAMPLE 39

N6-Benzoyl-2'-O-(2-phthalimido-N-hydroxyethyl)-3',5'-O-(1,1,3,3-tetraisopropyldisiloxane-1,3-diyl)adenosine To a solution of 2'-O-(2-Phthalimido-N-hydroxyethyl)-3', 5'-O-(1,1,3,3-tetraisopropyldisiloxane-1,3-diyl)adenosine (1.09 g, 1.97 mmol) in anhydrous pyridine (19 mL) cooled to 5° C. was added benzoyl chloride (1.14 mL, 9.8 mmol) and the resulting mixture was stirred at ambient temperature for 12 hours. After cooling the mixture to 5° C., cold water (3.8 mL) was added, the mixture was stirred for 15 minutes, and conc NH$_4$OH (3.8 mL) was added. After stirring for 30 minutes at 5° C. the solvent was evaporated to give a residue which was dissolved in water and extracted with CH$_2$Cl$_2$ three times. The organic extracts were combined, dried over MgSO$_4$, and evaporated in vacuo to afford an oil. The oil was purified by flash chromatography using hexanes-EtOAc, 50:50, then 20:80, to give the title compound as an oil (0.618 g, 48%).

$^1$H NMR (CDCl$_3$): δ 9.2 (br s, 1H), 8.69 (s, 1H), 8.27 (s, 1H), 8.0–7.4 (m, 9H), 6.12 (s, 1H), 4.95 (dd, J$_{1',2'}$=4.7 Hz, J$_{2',3'}$=9.1 Hz, 1H), 4.5–4.0 (m, 8H), 1.06 (m, 28H). $^{13}$C NMR (CDCl$_3$): δ 164.4, 163.3, 152.5, 150.8, 149.3, 142.1, 134.4, 133.7, 132.6, 132.1, 128.7, 128.2, 127.7, 123.4, 88.9, 82.7, 81.3, 77.5, 70.1, 69.6, 60.0, 17.2, 17.0, 16.8, 13.3, 12.8, 12.7, 12.6. LRMS (FAB+) m/z 803 (M+H).

EXAMPLE 40

N$^6$-Benzoyl-2'-O-(2-phthalimido-N-hydroxyethyl) adenosine

To a solution of N6-Benzoyl-2'-O-(2-phthalimido-N-hydroxyethyl)-3',5'-O-(1,1,3,3-tetraisopropyldisiloxane-1,3-diyl)adenosine (0.680 g, 0.847 mmol) in THF (20 mL) in a polyethylene reaction vessel at 5° C. was added HF-pyridine (70%, 0.48 mL, 16.9 mmol) and the resulting mixture was warmed to ambient temperature. After stirring for 12 hours the solvent was evaporated in vacuo, EtOAc was added, the solution was washed with water, and the aqueous layer was separated and extracted with EtOAc. The organic layers were combined, dried over MgSO$_4$, and the solvent was evaporated in vacuo to give the title compound as a solid (408 mg, 86%).

$^1$H NMR (DMSO-d$_6$): δ 11.2 (br s, 1H), 8.71 (s, 1H), 8.67 (s, 1H), 8.0–7.5 (m, 9H), 6.11 (d, J 1',2'=5.7 Hz), 5.23 (d, 1H), 5.14 (t, 1H), 4.66 (t, 1H), 4.35 (m, 3H), 3.90 (m, 3H), 3.6 (m, 2H). $^{13}$C NMR (DMSO-d$_6$): δ 163.5, 152.0, 143.2, 135.0, 132.6, 131.9, 131.7, 129.3, 128.7, 128.5, 123.4, 86.3, 85.8, 81.3, 76.8, 69.0, 68.7, 61.3. LRMS (FAB+) m/z: 561 (M+H, 583 (M+Na+).

EXAMPLE 41

N$^6$-Benzoyl-2'-O-(2-phthalimido-N-oxyethyl)-5'-O-(4,4'-dimethoxytrityl)adenosine To a solution of N$^6$-Benzoyl-2'-O-(2-phthalimido-N-hydroxyethyl)adenosine (0.258 g, 0.46 mmol) in anhydrous pyridine (5 mL) was added 4,4'-dimethoxytrityl chloride (0.179 g, 0.53 mmol) and the solution was stirred for 12 hours at ambient temperature. Water was added and the mixture was extracted with EtOAc three times. The organic extracts were combined, evaporated in vacuo, and dried over MgSO$_4$. The resulting oil was purified by flash chromatography using hexanes-EtOAc, 90:10, to give the title compound as an oil (0.249 g, 63%).

$^1$H NMR (CDCl$_3$): δ 9.16 (br s, 1H), 8.68 (s, 1H), 8.28 (s, 1H), 8.1–6.8 (m, 22H), 6.26 (d, J 1',2'=4.0 Hz, 1H), 4.76 (m, 1H), 4.60 (m, 1H), 4.4–4.3 (m, 3H), 4.13–4.0 (m, 3H), 3.77 (s, 6H), 3.48 (m, 2H). $^{13}$C NMR (CDCl$_3$): δ 164.5, 163.6, 158.5, 152.6, 151.4, 149.5, 144.5, 141.9, 135.7, 134.7, 132.7. 130.1, 128.8, 128.2, 127.8, 126.9, 123.7, 113.2, 87.2, 84.1, 82.6, 69.9, 69.0, 63.0, 60.3, 55.2. HRMS (FAB+) m/z (M+Cs+) calcd for C$_{48}$H$_{42}$N$_6$O$_{10}$ 995.2017, found 995.2053 (M+Cs+).

EXAMPLE 42

N$^6$-Benzoyl-2'-O-(2-phthalimido-N-oxyethyl)-5'-O-(4,4'-dimethoxytrityl)adenosine-3'-[(2-cyanoethyl)-N,N-diisopropylphosphoramidite]

To a solution of N$^6$-benzoyl-2'-O-(2-phthalimido-N-oxyethyl)-5'-O-(4,4'-dimethoxytrityl)adenosine (0.300 g, 0.348 mmol) in CH$_2$Cl$_2$ (10 mL) was added diisopropylamine tetrazolide (0.030 g, 0.174 mmol) and 2-cyanoethyl-N,N,N',N'-tetraisopropylphosphorodiamidite (0.13 mL, 0.418 mmol). After stirring for 12 hours at ambient temperature additional diisopropylamine tetrazolide (0.060 g, 0.348 mmol) and 2-cyanoethyl-N,N,N',N'-tetraisopropylphosphorodiamidite (0.26 mL, 0.832 mmol) were added in two portions over 24 hours. After 24 hours CH$_2$Cl$_2$—NEt$_3$, 100:1, was added and the mixture was washed with saturated aqueous NaHCO$_3$ and brine. The organic layer was separated, dried over MgSO$_4$, and the solvent was evaporated in vacuo. The resulting oil was purified by flash chromatography by pre-treating the silica with hexanes-EtOAc-NEt$_3$, (40:60:1), then using the same solvent system to give the title compound as an oil (203 g, 55%).

$^1$H NMR (CDCl$_3$): δ 6.27 (m, 1H). $^{31}$P NMR (CDCl$_3$): δ 151.0, 150.5. HRMS (FAB+) m/z (M+Cs+) calcd for C$_{57}$H$_{59}$N$_8$O$_{11}$P 1195.3095, found 1195.3046 (M+Cs+)

EXAMPLE 43

2'-O-(2-aminooxyethyl)-3',5'-O-(1,1,3,3-tetraisopropyldisiloxane-1,3-diyl)adenosine To a solution of 2'-O-(2-Phthalimido-N-hydroxyethyl)-3',5'-O-(1,1,3,3-tetraisopropyldisiloxane-1,3-diyl)adenosine (0.228 g, 0.326 mmol) in CH$_2$Cl$_2$ (5 mL) at 5° C. was added methylhydrazine (0.017 mL, 0.326 mmol) with stirring for 2 hours. The mixture was filtered to remove a precipitate and the filtrate was washed with water and brine. The organic layer was separated, dried over MgSO$_4$, and the evaporated in vacuo to give the title compound as an oil (186 mg). The oil was of sufficient purity for subsequent reactions.

$^1$H NMR (CDCl$_3$): δ 8.31 (s, 1H), 8.15 (s, 1H), 6.07 (s, 1H), 5.78 (br s, 2H), 4.70 (dd, J 1',2'=4.4 Hz, J 2',3'=9.0 Hz, 1H), 4.3–3.9 (m, 8H), 1.9 (br, 2H), 1.0 (m, 28H).

LRMS (FAB+) m/z: 569 (M+H), 702 (M+Cs+)

EXAMPLE 44

2'-O-(2-O-Formaldoximylethyl)-3',5'-O-(1,1,3,3-tetraisopropyldisiloxane-1,3-diyl)adenosine To a solution of 2'-O-(2-aminooxyethyl)-3',5'-O-(1,1,3,3-tetraisopropyldisiloxane-1,3-diyl)adenosine (0.186 g, 0.326 mmol) in EtOAc (2 mL) and MeOH (2 mL) was added formaldehyde (aqueous 37%, 0.028 mL, 0.342 mmol) with stirring at ambient temperature for 3 hours. The solvent was evaporated in vacuo to give the title compound as an oil (189 mg). The oil was of sufficient purity for subsequent reactions.

$^1$H NMR (CDCl$_3$): δ 8.31 (s, 1H), 8.09 (s, 1H), 6.97 (d, J=8.3 Hz, 1H), 6.38 (d, J=8.3 Hz, 1H), 6.01 (s, 1H), 5.66 (br s, 2H), 4.77 (dd, J$_{1',2'}$=4.7 Hz, J$_{,3'}$=9.3 Hz), 4.3–4.0 (m, 8H), 1.0 (m, 28H). LRMS (FAB+) m/z: 581 (M+H), 713 (M+Cs+)

EXAMPLE 45

N$^6$-Benzoyl-2'-O-(2-O-formaldoximylethyl)-3',5'-O-(1,1,3,3-tetraisopropyldisiloxane-1,3-diyl)adenosine To a solution of 2'-O-(2-O-Formaldoximylethyl)-3',5'-β-(1,1,3,3-tetraisopropyldisiloxane-1,3-diyl)adenosine (0.189 g, 0.326 mmol) in pyridine (5 mL) at 5° C. was added benzoyl chloride (0.19 mL, 1.63 mmol) and the resulting solution was stirred at ambient temperature for 3 hours. The solution was cooled to 5° C. and concentrated NH$_4$OH (1.5 mL) was added with stirring for 1 hour. The solvent was evaporated in vacuo to give an oil which was dissolved in CH$_2$Cl$_2$. The solution was washed with water and the organic layer was separated, dried with MgSO$_4$, and the solvent was evaporated to give the title compound (223 mg) as an oil which was of sufficient purity for subsequent reactions.

$^1$H NMR (CDCl$_3$): δ 9.30 (br, 1H), 8.79 (s, 1H), 8.31 (s, 1H), 8.1–7.2 (m, 5H), 7.00 (d, 1H), 6.39 (d, 1H), 6.09 (s, 1H), 4.77 (dd, 1H), 4.4–3.9 (m, 8H), 1.1 (m, 28H).

EXAMPLE 46

N$^6$-Benzoyl-2'-O-(2-O-formaldoximylethyl) adenosine

To a solution of N$^6$-benzoyl-2'-o-(2-O-formaldoximylethyl)-3',5'-O-(1,1,3,3-tetraisopropyldisiloxane-1,3-diyl)adenosine (223 mg, 0.326 mmol) in THF (10 mL) in a polyethylene reaction vessel at 5° C. was added HF-pyridine (70%, 0.19 mL, 6.5 mmol) and the mixture was allowed to warm to ambient temperature. After stirring for 48 hours the solvents were evaporated in vacuo to give a residue which was dissolved in EtOAc and washed with water. The organic layer was separated, the aqueous layer was extracted with EtOAc, and the organic layers were combined, dried over MgSO$_4$, and evaporated in vacuo. The resulting residue was purified by flash chromatography using EtOAc-MeOH, 95:5, to give the title compound as a solid (24 mg, 17%).

$^1$H NMR (CDCl$_3$); δ 9.05 (br s, 1H), 8.77 (s, 1H), 8.13 (s, 1H), 7.9–7.2 (m), 6.26 (d, J=10.7 Hz, 1H), 6.03 (d, J$_{1',2'}$=7.8 Hz), 4.88 (dd, J=4.6 Hz, J=7.9 Hz, 1H), 4.6–3.7 (m, 10H). LRMS (FAB+) m/z: 443 (M+H). LRMS (FAB−) m/z: 441 (M−H).

EXAMPLE 47

N6-Benzoyl-2'-O-(2-O-formaldoximylethyl)-5'-O-(4,4'-dimethoxytrityl)adenosine

To a solution of N$^6$-benzoyl-2'-O-(2-O-formaldoximylethyl)adenosine (0.34 g, 0.768 mmol) in pyridine (7 mL) was added 4,4'-dimethoxytrityl chloride (0.312 g, 0.922 mmol) and the reaction mixture was stirred at ambient temperature for 5 hours. Additional amounts of 4,4'-dimethoxytrityl chloride (520 mg, 1.54 mmol and 340 mg, 0.768 mmol) were added over 24 hours. The solvent was evaporated, the crude product was dissolved in EtOAc, and washed with water. The organic layer was separated, dried over MgSO$_4$ and the solvent was evaporated in vacuo. The crude material was purified by column chromatography using EtOAc-Hexanes-NEt$_3$, 80:20:0.5, v/v/v, followed by, EtOAc-NEt3, 100:0.5, v/v, as solvent to give the title compound as an oil (0.269 g, 47%).

$^1$H NMR (CDCl$_3$): δ 8.99 (br s, 1H), 8.74 (s, 1H), 8.1–6.8 (m, 18H), 7.00 (d, 1H), 6.43 (d, 1H), 6.19 (d, 1H), 4.72 (m, 1H), 4.48 (m, 1H), 4.23 (m, 3H), 4.1 (m, 1H), 3.9 (m, 1H), 3.78 (s, 6H), 3.45 (m, 2H), 3.15 (d, 1H). HRMS (FAB+) m/z (M+Cs+) calcd for C$_{41}$H$_{40}$N$_6$O$_8$ 877.1962, found 877.1988 (M+Cs+).

EXAMPLE 48

2'-O-Allyl-5'-O-dimethoxytrityl-5-methyluridine

In a 100 mL stainless steel pressure reactor, allyl alcohol (20 mL) was slowly added to a solution of borane in tetrahydrofuran (1 M, 10 mL, 10 mmol) with stirring. Hydrogen gas rapidly evolved. Once the rate of bubbling subsided, 2,2'-anhydro-5-methyluridine (1.0 g, 0.4.2 mmol) and sodium bicarbonate (6 mg) were added and the reactor was sealed. The reactor was placed in an oil bath and heated to 170° C. internal temperature for 18 hours. The reactor was cooled to room temperature and opened. Tlc revealed that all the starting material was gone (starting material and product Rf 0.25 and 0.60 respectively in 4:1 ethyl acetate/methanol on silica gel). The crude solution was concentrated, coevaporated with methanol (50 mL), boiling water (15 mL), absolute ethanol (2×25 mL) and then the residue was dried to 1.4 g of tan foam (1 mm Hg, 25° C., 2 hours). A portion of the crude nucleoside (1.2 g) was used for the next reaction step without further purification. The residue was coevaporated with pyridine (30 mL) and redissolved in pyridine (30 mL). Dimethoxytrityl chloride (1.7 g, 5.0 mmol) was added in one portion at room temperature. After 2 hours the reaction was quenched with methanol (5 mL), concentrated in vacuo and partitioned between a solution of saturated sodium bicarbonate and ethyl acetate (150 mL each). The organic phase was separated, concentrated and the residue was subjected to column chromatography (45 g silica gel) using a solvent gradient of hexanes-ethyl acetate-triethylamine (50:49:1) to (60:39:1). The product containing fractions were combined, concentrated, coevaporated with acetonitrile (30 mL) and dried (1 mm hg, 25° C., 24 hours) to 840 mg (34% two-step yield) of white foam solid. The NMR was consistent with the unmethylated uridine analog reported in the literature.

EXAMPLE 49

2'-O-(2-hydroxyethyl)-5'-O-dimethoxytrityl-5-methyluridine

2'-O-Allyl-5'-O-dimethoxytrityl-5-methyluridine (1.0 g, 1.6 mmol), aqueous osmium tetroxide (0.15 M, 0.36 mL, 0.0056 mmol, 0.035 eq) and 4-methylmorpholine N-oxide (0.41 g, 3.5 mmol, 2.15 eq) were dissolved in dioxane (20 mL) and stirred at 25° C. for 4 hours. Tlc indicated complete and clean reaction to the diol (Rf of starting to diol 0.40 to 0.15 in dichloromethane/methanol 97:3 on silica). Potassium periodate (0.81 g, 3.56 mmol, 2.2 eq) was dissolved in water (10 mL) and added to the reaction. After 17 hours the tlc indicated a 90% complete reaction (aldehyde Rf 0.35 in system noted above). The reaction solution was filtered, quenched with 5% aqueous sodium bisulfite (200 mL) and the product aldehyde was extracted with ethyl acetate (2×200 mL). The organic layers were combined, washed with brine (2×100 mL) and concentrated to an oil. The oil was dissolved in absolute ethanol (15 mL) and sodium borohydride (1 g) was added. After 2 hours at 25° C. the tlc indicated a complete reaction. Water (5 mL) was added to destroy the borohydride. After 2 hours the reaction was stripped and the residue was partitioned between ethyl acetate and saturated sodium bicarbonate solution (50 mL each). The organic layer was concentrated in vacuo and the residue was columned (silica gel 30 g, dichloromethane-methanol 97:3). The product containing fractions were combined and stripped and dried to 0.50 g (50%) of white foam. The NMR was consistent with that of material prepared by the glycosylation route.

EXAMPLE 50

2'-O-(2-hydroxyethyl)-5-methyluridine

In a 100 mL stainless steel pressure reactor, ethylene glycol (20 mL) was slowly added to a solution of borane in tetrahydrofuran (1 M, 10 mL, 10 mmol) with stirring. Hydrogen gas rapidly evolved. Once the rate of bubbling subsided, 2,2'-anhydro-5-methyluridine (1.0 g, 0.4.2 mmol) and sodium bicarbonate (3 mg) were added and the reactor was sealed. The reactor was placed in an oil bath and heated to 150° C. internal temperature for 72 hours. The bomb was cooled to room temperature and opened. TLC revealed that 65% of the starting material was gone (starting material and product Rf 0.25 and 0.40 respectively in 4:1 ethyl acetate/methanol on silica gel). The reaction was worked up incomplete. The crude solution was concentrated (1 mm Hg at 100° C., coevaporated with methanol (50 mL), boiling water (15 mL) and absolute ethanol (2×25 mL) and the residue was dried to 1.3 g of off-white foam (1 mm Hg, 25° C., 2 hours). NMR of the crude product was consistent with 65% desired product and 35% starting material. The TLC Rf matched (on cospot) the same product generated by treating the DMT derivative above with dilute hydrochloric acid in methanol as well as the Rf of one of the spots generated by treating a sample of this product with dimethoxytrityl chloride matched the known DMT derivative (other spots were DMT on side chain and bis substituted product).

EXAMPLE 51

N4-benzoyl-2'-O-(2-phthalimido-N-oxyethyl)-5'-O-(4,4'-dimethoxytrityl)cytidine-3'-[(2-cyanoethyl)-N, N-diisopropylphosphoramidite]

The 2'-O-aminooxyethyl cytidine and guanosine analogs may be prepared via similar chemistry in combination with reported literature procedures. Key to the synthetic routes is the selective 2'-O-alkylation of unprotected nucleosides. (Guinosso, C. J., Hoke, G. D., Frier, S., Martin, J. F., Ecker, D. J., Mirabelli, C. K., Crooke, S. T., Cook, P. D., *Nucleosides Nucleotides*, 1991, 10, 259; Manoharan, M., Guinosso, C. J., Cook, P. D., *Tetrahedron Lett.*, 1991, 32, 7171; Izatt, R. M., Hansen, L. D., Rytting, J. H., Christensen, J. J., *J. Am. Chem. Soc.*, 1965, 87, 2760. Christensen, L. F., Broom, A. D., *J. Org. Chem.*, 1972, 37, 3398. Yano, J., Kan, L. S., Ts'o, P. O. P., *Biochim. Biophys. Acta*, 1980, 629, 178; Takaku, H., Kamaike, K., *Chemistry Lett.* 1982, 189). Thus, cytidine may be selectively alkylated to afford the intermediate 2'-O-(2-ethylacetyl)-cytidine. The 3'-isomer of 2'-O-(2-ethylacetyl)cytidine is typically present in a minor amount and can be resolved by chromatography or crystallization. 2'-O-(2-ethylacetyl)-cytidine can be protected to give 2'-O-(2-ethylacetyl)-5'-O-(4,4'-dimethoxytrityl)cytidine which upon reduction gives 2'-O-(2-hydroxyethyl)-5'-O-(4,4'-dimethoxytrityl)cytidine. This compound is further N-4-benzoylated, the primary hydroxyl group may be displaced by N-hydroxyphthalimide via a Mitsunobu reaction, and the protected nucleoside may be phosphitylated as usual to yield N4-benzoyl-2'-O-(2-phthalimido-N-oxyethyl)-5'-O-(4,4'-dimethoxytrityl)cytidine-3'-[(2-cyanoethyl)-N,N-diisopropylphosphoramidite].

EXAMPLE 52

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

In a similar fashion to the previous example the 2'-O-aminooxyethyl guanosine analog may be obtained by selective 2'-O-alkylation of diaminopurine riboside (multigram quantities of diaminopurine riboside may be purchased from Schering AG (Berlin) to provide 2'-O-(2-ethylacetyl) diaminopurine riboside along with a minor amount of the 3'-O— isomer. The 2'-O-(2-ethylacetyl)diaminopurine riboside is resolved and converted to 2'-O-(2-ethylacetyl) guanosine by treatment with adenosine deaminase. (McGee, D. P. C., Cook, P. D., Guinosso, C. J., *PCT Int. Appl.*, 85 pp.; PIXXD2; WO 94/02501 A1 940203.) Standard protection procedures should afford 2'-O-(2-ethylacetyl)-5'-O-(4,4'-dimethoxytrityl)guanosine and 2N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As illustrated above the hydroxyl group may be displaced by N-hydroxyphthalimide via a Mitsunobu reaction, and the protected nucleoside may phosphitylated to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

EXAMPLES 53–85

Procedures for the Preparation of Compounds of the Formula:

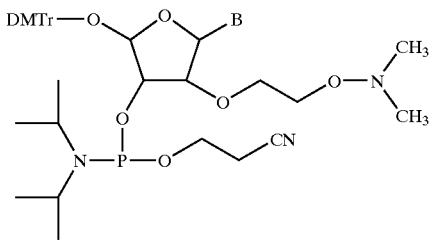

wherein:
B is a heterocyclic base moiety and DMTr is dimethoxytrityl.

EXAMPLE 53

5'-O-tert-Butyldiphenylsilyl-O²-2'-anhydro-5-methyluridie

O₂-2'-anhydro-5-methyluridine (Pro. Bio. Sint., Varese, Italy, 100 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 hours at ambient temperature. TLC (Rf 0.22, ethyl acetate) indicated a complete reaction. The solution was concentrated under reduced pressure to a thick oil. This was partitioned between dichloromethane (1 L) and sat'd sodium bicarbonate (2×1'-L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

EXAMPLE 54

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL. In the fume hood and with manual stirring, ethylene glycol (350 mL, excess) was added cautiously at first until the evolution of hydrogen gas subsided. 5'-O-tert-Butyldiphenylsilyl-O²-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 hours (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

NMR (DMSO-d₆) d 1.05 (s, 9H, t-butyl), 1.45 (s, 3H, CH3), 3.5–4.1 (m, 8H, CH2CH2, 3'-H, 4'-H, 5'-H, 5"-H), 4.25 (m, 1H, 2'-H), 4.80 (t, 1H, CH₂O—H), 5.18 (d, 2H, 3'-OH), 5.95 (d, 1H, 1'-H), 7.35–7.75 (m, 11H, Ph and C6-H), 11.42 (s, 1H, N—H).

EXAMPLE 55

2'-O-([2-phthalimidoxy)ethyl]-5'-t-butyldiphenylsilyl-5-methyluridine

Nucleoside 5'-O-tert-butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P₂O₅ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get the title compound as white foam (21.819, 86%). Rf 0.56 (ethyl acetate:hexane, 60:40). MS (FAB⁻)m/e 684 (M–H⁺)

EXAMPLE 56

5'-O-tert-butyldiphenylsilyl-2'-O-[(2-formadoximinooxy)ethyl]-5-methyluridine

2'-O-([2-Phthalimidoxy)ethyl]-5'-t-butyldiphenylsilyl-5-methyluridine (3.1 g, 4.5 mmol) was dissolved in dry CH₂Cl₂ (4.5 mL) and methylhydrazine (300 mL, 4.64 mmol) was added dropwise at −10° C. to 0° C. After 1 hr the mixture was filtered, the filtrate was washed with ice cold CH₂Cl₂ and the combined organic phase was washed with water, brine and dried over anhydrous $Na_2SO_4$. The solution concentrated to get 2'-O-(aminooxyethyl) thymidine, which was then dissolved in MeOH (67.5 mL). To this formaldehyde (20% aqueous solution, w/w, 1.1eg.) was added and the mixture for 1 hr. Solvent removed under vacuum; residue chromatographed to get the title compound as white foam (1.95, 78%). Rf 0.32 (5% MeOH in $CH_2Cl_2$). MS (Electrospray$^-$) m/e 566 (M–H$^\oplus$)

EXAMPLE 57

5'-O-tert-Butyldiphenylsilyl-2'-O-[N,N-dimethylaminooxyethyl]-5-methyluridine 5'-O-tert-Butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodiumcyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase dried over anhydrous $Na_2SO_4$, evaporated to dryness. Residue dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodiumcyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$; and evaporated to dryness. The residue obtained was purified by flash column chromatography and eluted with 5% MeOH in $CH_2Cl_2$ to get the title compound as a white foam (14.6 g, 80%). Rf 0.35 (5% MeOH in $CH_2Cl_2$) MS (FAB$^\oplus$) m/e 584 (M+H$^\oplus$)

EXAMPLE 58

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent removed under vacuum and the residue placed on a flash column and eluted with 10% MeOH in $CH_2Cl_2$ to get the title compound (766 mg, 92.5%). Rf 0.27 (5% MeOH in $CH_2Cl_2$). MS (FAB$^\oplus$) m/e 346 (M+H$^\oplus$)

EXAMPLE 59

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get the title compound (1.13 g, 80%). Rf 0.44 ((10% MeOH in $CH_2Cl_2$). MS (FAB$^\oplus$) m/e 648 (M+H$^\oplus$)

EXAMPLE 60

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get the title compound as a foam (1.04 g, 74.9%). Rf 0.25 (ethyl acetate:hexane, 1:1).

$^{31}$P NMR (CDCl$_3$) δ 150.8 ppm; MS (FAB$^\oplus$) m/e 848 (M+H$^\oplus$)

EXAMPLE 61

2'/3'-O-allyl adenosine

Adenosine (20 g, 74.84 mmol) was dried over $P_2O_5$ under high vacuum at 40° C. for two days. It was then suspended in DMF under inert atmosphere. Sodium hydride (2.5 g, 74.84 mmol, 60% dispersion in mineral oil), stirred at room temperature for 10 minutes. Then allyl bromide (7.14 mL, 82.45 mmol) was added dropwise and the reaction mixture was stirred at room temperature overnight. DMF was removed under vacuum and residue was washed with ethyl acetate (100 mL). Ethyl acetate layer was decanted. Filtrate obtained contained product. It was then placed on a flash column and eluted with 10% MeOH in $CH_2Cl_2$ to get the title compound (15.19 g, 66%). Rf 0.4, 0.4a ((10% MeOH in $CH_2Cl_2$)

EXAMPLE 62

2'/3'-O-allyl-N$^6$-benzoyl adenosine

2'/3'-O-allyl adenosine (15.19 g, 51.1 mmol) was dried over $P_2O_5$ under high vacuum overnight at 40° C. It was then dissolved in anhydrous pyridine (504.6 mL) under inert atmosphere. Trimethylchlorosilane (32.02 mL, 252.3 mmol) was added at 0° C. and the reaction mixture was stirred for 1 hr under inert atmosphere. Then benzoyl chloride (29.4 mL, 252.3 mmol) was added dropwise. Once the addition of benzoyl chloride was over, the reaction mixture was brought to room temperature and stirred for 4 hrs. Then the reaction mixture was brought to 0° C. in an ice bath. Water (100.9 mL) was added and the reaction mixture was stirred for 30 minutes. Then NH$_4$OH (100.0 mL, 30% aqueous solution w/w) was added, keeping the reaction mixture at 0° C. and stirring for an additional 1 hr. Solvent evaporated residue partitioned between water and ether. Product precipitates as an oil, which was then chromatographed (5% MeOH in CH$_2$Cl$_2$) to get the title compound as a white foam (12.67 g, 62%).

EXAMPLE 63

3'-O-allyl-5'-O-tert-butyldiphenylsilyl-N$^6$-benzoyl-adenosine

2'/3'-O-allyl-N$^6$-benzoyl adenosine (11.17 g, 27.84 mmol) was dried over P$_2$O$_5$ under vacuum at 40° C., then dissolved in dry CH$_2$Cl$_2$ (56 mL, sure seal from Aldrich). 4-dimethylaminopyridine (0.34 g, 2.8 mmol), triethylamine (23.82 mL, 167 mmol) and t-butyldiphenylsilyl chloride were added. The reaction mixture was stirred vigorously for 12 hr. Reaction was monitored by TLC (ethyl acetate:hexane 1:1). It was then diluted with CH$_2$Cl$_2$ (50 mL) and washed with water (3×30 mL). Dichloromethane layer was dried over anhydrous Na$_2$SO$_4$ and evaporated to dryness. Residue purified by flash chromatography (ethyl acetate:hexane 1:1 as eluent) to get the title compound as a white foam (8.85 g, 49%). Rf 0.35 (ethyl acetate:hexane, 1:1)

EXAMPLE 64

5'-O-tert-butyldiphenylsilyl-N$^6$-benzoyl-2'-O-(2,3-dihydroxypropyl)-adenosine

3'-O-allyl-5'-O-tert-butyldiphenylsilyl-N$^6$-benzoyl-adenosine (5.5 g, 8.46 mmol), 4-methylmorpholine N-oxide (1.43 g, 12.18 mmol) were dissolved in dioxane (45.42 mL). 4% aqueous solution of OSO$_4$ (1.99 mL, 0.31 mmol) was added. The reaction mixture was protected from light and stirred for 3 hrs. Reaction was monitored by TLC (5% MeOH in CH$_2$Cl$_2$). Ethyl acetate (100 mL) was added and the resulting reaction mixture was washed with water (1×50 mL). Ethyl acetate layer was dried over anhydrous Na$_2$SO$_4$ and evaporated to get the title compound (5.9 g) and used for next step without purification. Rf 0.17 (5% MeOH in CH$_2$Cl$_2$)

EXAMPLE 65

5'-O-tert-butyldiphenylsilyl-N$^6$-benzoyl-2'-O-(formylmethyl)-adenosine

5'-O-tert-butyldiphenylsilyl-N$^6$-benzoyl-2'-O-(2,3-dihydroxypropyl)-adenosine (5.59 g, 8.17 mmol) was dissolved in dry CH$_2$Cl$_2$ (40.42 mL). To this NaIO$_4$ adsorbed on silica gel (Ref. *J. Org. Chem.* 1997, 62, 2622–2624) (16.34 g, 2 g/mmol) was added and stirred at ambient temperature for 30 minutes. Reaction monitored by TLC (5% MeOH in CH$_2$Cl$_2$). Reaction mixture was filtered and the filtrate washed thoroughly with CH$_2$Cl$_2$. Dichloromethane layer evaporated to get the title compound (5.60 g) that was used in the next step without purification. Rf 0.3 (5% MeOH in CH$_2$Cl$_2$)

EXAMPLE 66

5'-O-tert-butyldiphenylsilyl-N$^6$-2'-O-(2-hydroxyethyl)adenosine

5'-O-tert-butyldiphenylsilyl-N$^6$-benzoyl-2'-O-(formylmethyl)-adenosine (5.55 g, 8.50 mmol) was dissolved in a solution of 1M pyridinium p-toluenesulfonate in anhydrous MeOH (85 mL). Reaction mixture was protected from moisture. Sodiumcyanoborohydride (1.08 g, 17.27 mmol) was added and reaction mixture stirred at ambient temperature for 5 hrs. The progress of the reaction was monitored by TLC (5% MeOH in CH$_2$Cl$_2$). The reaction mixture was diluted with ethyl acetate (150 mL), then washed with 5% NaHCO$_3$ (75 mL) and brine (75 mL). Ethyl acetate layer was dried over anhydrous Na$_2$SO$_4$ and evaporated to dryness. Residue purified by flash chromatography (5% MeOH in CH$_2$Cl$_2$) to get the title compound (4.31 g, 77.8%). Rf 0.21 (5% MeOH in CH$_2$Cl$_2$). MS (FAB$^\oplus$) m/e 655 (M+H$^\oplus$), 677 (M+Na$^\oplus$)

EXAMPLE 67

5'-tert-butyldiphenylsilyl-N$^6$-benzoyl-2-O-(2-phthalimido-oxyethyl) adenosine

5'-O-tert-butyldiphenylsilyl-N$^6$-benzoyl-2'-O-(formylmethyl)-adenosine (3.22 g, 4.92 mmol) was mixed with triphenylphosphine (1.55 g, 5.90 mmol) and N-hydroxyphthalimide (0.96 g, 5.90 mmol). It was then dried over P$_2$O$_5$ under vacuum at 40° C. for two days. Dissolved dried mixture in anhydrous THF (49.2 mL) under inert atmosphere. Diethyl azodicarboxylate (0.93 mL, 5.90 mmol) was added dropwise. The rate of addition was maintained such that resulting deep red coloration is just discharged before adding the next drop. After the addition was completed, the reaction was stirred for 4 hrs, monitored by TLC (ethylacetate:hexane 70:30). Solvent was removed under vacuum and the residue dissolved in ethyl acetate (75 mL). The ethyl acetate layer was washed with water (75 mL), then dried over Na$_2$SO$_4$, concentrated and chromatographed (ethylacetate:hexane 70:30) to get the title compound (3.60 g, 91.5%). Rf 0.27 ethyl acetate:hexane, 7:3) MS (FAB$^\oplus$) m/e 799 (M+H$^\oplus$), 821 (M+Na$^\oplus$)

EXAMPLE 68

5'-O-tert-butyldiphenylsilyl-N$^6$-benzoyl-2'-O-(2-formaldoximinooxyethyl) adenosine 5'-tert-Butyldiphenylsilyl-N$^6$-benzoyl-2'-O-(2-phthalimidooxyethyl) adenosine (3.5 g, 4.28 mmol) was dissolved in CH$_2$Cl$_2$ (43.8 mL). N-methylhydrazine (0.28 mL, 5.27 mmol) was added at −10° C. and the reaction mixture was stirred for 1 hr at −10 to 0° C. Reaction monitored by TLC (5% MeOH in CH$_2$Cl$_2$). A white precipitate formed was filtered and filtrate washed with ice cold CH$_2$Cl$_2$ thoroughly. Dichloromethane layer evaporated on a rotavapor keeping the water bath temperature of rotavapor at less than 25° C. Residue obtained was then dissolved in MeOH (65.7 mL). Formaldehyde (710 mL, 4.8 mmol, 20% solution in water) was added and the reaction mixture was stirred at ambient temperature for 1 hr. Reaction monitored by $^1$H NMR. Reaction mixture concentrated and chromatographed (5% MeOH in CH$_2$Cl$_2$) to get the title compound as a white foam (2.47 g, 83%). Rf 0.37 (5% MeOH in CH$_2$Cl$_2$). MS (FAB$^\oplus$) m/e 681 (M+H$^\oplus$)

EXAMPLE 69

5'-tert-butyldiphenylsilyl-N$^6$-benzoyl-2'-O-(2-N,N-dimethylaminooxyethyl)adenosine 5'-O-tert-butyldiphenylsilyl-N$^6$-benzoyl-2'-O-(2-formaldoximinooxyethyl) adenosine (2.2 g, 3.23 mmol) was dissolved in a solution of 1M pyridinium p-toluenesulfonate (PPTS) in MeOH (32 mL). Reaction protected from moisture. Sodium cyanoborohydride (0.31 g) was added at 10° C. and reaction mixture was stirred for 10 minutes at 10° C. It was then brought to ambient temperature and stirred for 2 hrs, monitored by TLC (5% MeOH in $CH_2Cl_2$). 5% aqueous sodiumbicarbonate (100 mL) and extracted with ethyl acetate (3×50 mL). Ethyl acetate layer was dried over anhydrous $Na_2SO_4$ and evaporated to dryness. Residue was dissolved in a solution of 1M PPTS in MeOH (32 mL). Formaldehyde (0.54 mL, 3.55 mmol, 20% aqueous solution) was added and stirred at room temperature for 10 minutes. Sodium cyanoborohydride (0.31 g) was added at 10° C. and stirred for 10 minutes at 10° C. Then the reaction mixture was removed from ice bath and stirred at room temperature for an additional 2 hrs, monitored by TLC (5% MeOH in $CH_2Cl_2$). Reaction mixture was diluted with 5% aqueous $NaHCO_3$ (100 mL) and extracted with ethyl acetate (3×50 mL). Ethyl acetate layer was dried, evaporated and chromatographed (5% MeOH in $CH_2Cl_2$) to get the title compound (1.9 g, 81.8%). Rf 0.29 (5% MeOH in $CH_2Cl_2$) MS ($FAB^\oplus$) m/e 697 ($M+H^\oplus$), 719 ($M+^{60}$)

EXAMPLE 70

$N^6$-benzoyl-2'-O-(N,N-dimethylaminooxyethyl) adenosine

To a solution of $Et_3N$-3HF (1.6 g, 10 mmol) in anhydrous THF (10 mL) triethylamine (0.71 mL, 5.12 mmol) was added. Then this mixture was added to 5'-tert-butyldiphenylsilyl-$N^6$-benzoyl-2'-O-(2-N,N-dimethylaminooxyethyl) adenosine (0.72 g, 1 mmol) and stirred at room temperature under inert atmosphere for 24 hrs. Reaction monitored by TLC (10% MeOH in $CH_2Cl_2$). Solvent removed under vacuum and the residue chromatographed (10% MeOH in $CH_2Cl_2$) to get the title compound (0.409 g, 89%). Rf 0.40 (10% MeOH in $CH_2Cl_2$). MS ($FAB^\oplus$) m/e 459 ($M+H^\oplus$).

EXAMPLE 71

5'-O-dimethoxytrityl-$N^6$-benzoyl-2'-O-(2-N,N-dimethylamino-oxyethyl)adenosine $N^6$-benzoyl-2'-O—(N,N-dimethylaminooxyethyl) adenosine 0.4 g, 0.87 mmol) was dried over $P_2O_5$ under vacuum overnight at 40° C. 4-dimethylaminopyridine (0.022 g, 0.17 mmol) was added. Then it was co-evaporated with anhydrous pyridine (9 mL). Residue was dissolved in anhydrous pyridine (2 mL) under inert atmosphere, and 4,4'-dimethoxytrityl chloride (0.58 g, 1.72 mmol) was added and stirred at room temperature for 4 hrs. TLC (5% MeOH in $CH_2Cl_2$) showed the completion of the reaction. Pyridine was removed under vacuum, residue dissolved in $CH_2Cl_2$ (50 mL) and washed with aqueous 5% $NaHCO_3$ (30 mL) solution followed by brine (30 mL). $CH_2Cl_2$ layer dried over anhydrous $Na_2SO_4$ and evaporated. Residue chromatographed (5% MeOH in $CH_2Cl_2$ containing a few drops of pyridine) to get the title compound (0.5 g, 75%). Rf 0.20 (5% MeOH in $CH_2Cl_2$). MS (Electrospray$^-$) m/e 759 ($M+H^\oplus$)

EXAMPLE 72

$N^6$-benzoyl-5'-O-DMT-2'-O-(N,N-dimethylaminooxyethyl)adenosine-3'-O-phosphoramidite $N^6$-benzoyl-2'-O-(N,N-dimethylaminooxyethyl) adenosine (0.47 g, 0.62 mmol) was co-evaporated with toluene (5 mL). Residue was mixed with N,N-diisopropylamine tetrazolide (0.106 g, 0.62 mmol) and dried over $P_2O_5$ under high vacuum overnight. Then it was dissolved in anhydrous $CH_3CN$ (3.2 mL) under inert atmosphere. 2-cyanoethyl-tetraisopropyl phosphordiamidite (0.79 mL, 2.48 mmol) was added dropwise and the reaction mixture was stirred at room temperature under inert atmosphere for 6 hrs. Reaction was monitored by TLC (ethyl acetate containing a few drops of pyridine). Solvent was removed, then residue was dissolved in ethyl acetate (50 mL) and washed with 5% aqueous $NaHCO_3$ (2×25 mL). Ethyl acetate layer was dried over anhydrous $Na_2SO_4$, evaporated, and residue chromatographed (ethyl acetate containing a few drops of pyridine) to get the title compound (0.45 g, 76%). MS (Electrospray$^-$) m/e 959 ($M+H^\oplus$) $^{31}$P NMR ($CDCl_3$) δ 151.36, 150.77 ppm

EXAMPLE 73

2'/3'-O-allyl-2,6-diaminopurine riboside 2,6-Diaminopurine riboside (30 g, 106.4 mmol) was suspended in anhydrous DMF (540 mL). Reaction vessel was flushed with argon. Sodium hydride (3.6 g, 106.4 mmol, 60% dispersion in mineral oil) was added and the reaction stirred for 10 min. Allyl bromide (14.14 mL, 117.22 mmol) was added dropwise over 20 min. The resulting reaction mixture stirred at room temperature for 20 hr. TLC (10% MeOH in $CH_2Cl_2$) showed complete disappearance of starting material. DMF was removed under vacuum and the residue absorbed on silica was placed on a flash column and eluted with 10% MeOH in $CH_2Cl_2$. Fractions containing mixture of 2' and 3' allylated product was pooled together and concentrated to dryness to yield a mixture of the title compounds (26.38 g, 77%). Rf 0.26, 0.4 (10% MeOH in $CH_2Cl_2$)

EXAMPLE 74

2'-O-allyl-guanosine

A mixture of 2'/3'-O-allyl-2,6-diaminopurine riboside (20 g, 62.12 mmol) was suspended in 100 mm sodium phosphate buffer (pH 7.5) and adenosine deaminase (1 g) was added. The resulting solution was stirred very slowly for 60 hr, keeping the reaction vessel open to atmosphere. Reaction mixture was then cooled in ice bath for one hr and the precipitate obtained was filtered, dried over $P_2O_5$ under high vacuum to yield the title compound as white powder (13.92 g, 69.6% yield). Rf 0.19 (20% MeOH in $CH_2Cl_2$)

EXAMPLE 75

2'-O-allyl-3',5'-bis(tert-butyl diphenylsilyl)guanosine

2'-O-allyl-guanosine (6 g, 18.69 mmol) was mixed with imidazole (10.18 g, 14.952 mmol) and was dried over $P_2O_5$ under high vacuum overnight. It was then flushed with argon. Anhydrous DMF (50 mL) was added and stirred with the reaction mixture for 10 minutes. To this tert-butyldiphenylsilyl chloride (19.44 mL, 74.76 mmol) was added and the reaction mixture stirred overnight under argon atmosphere. DMF was removed under vacuum and the residue was dissolved in ethyl acetate (100 mL) and washed with water (2×75 mL). Ethyl acetate layer was dried over anhydrous $Na_2SO_4$ and evaporated to dryness. Residue placed on a flash column and eluted with 5% MeOH in $CH_2Cl_2$. Fractions containing the product were pooled together and evaporated to give the title compound (10.84 g, 72% yield) as a white foam. Rf=? MS ($FAB^\oplus$) m/e 800 ($M+H^\oplus$), 822 ($M+Na^\oplus$)

EXAMPLE 76

2'-O-(2-hydroxyethyl)-3',5'-bis(tert-butyldiphenylsilyl)guanosine

2'-O-allyl-3',5'-bis(tert-butyl diphenylsilyl)guanosine (9 g, 11.23 mmol) was dissolved in $CH_2Cl_2$ (80 mL). To the clear solution acetone (50 mL), 4-methyl morpholine-N-oxide (1.89 g, 16.17 mmol) was added. The reaction flask was protected from light. Thus 4% aqueous solution of osmium tetroxide was added and the reaction mixture was stirred at room temperature for 6 hr. Reaction volume was concentrated to half and ethyl acetate (50 mL) was added. It was then washed with water (30 mL) and brine (30 mL). Ethyl acetate layer was dried over anhydrous $Na_2SO_4$ and evaporated to dryness. Residue was then dissolved in $CH_2Cl_2$ and $NaIO_4$ adsorbed on silica (21.17 g, 2 g/mmol) was added and stirred with the reaction mixture for 30 min. The reaction mixture was filtered and silica was washed thoroughly with $CH_2Cl_2$. Combined $CH_2Cl_2$ layer was evaporated to dryness. Residue was then dissolved in dissolved in 1M pyridinium-p-toluene sulfonate (PPTS) in dry MeOH (99.5 mL) under inert atmosphere. To the clear solution sodium cyanoborohydride (1.14 g, 18.2 mmol) was added and stirred at room temperature for 4 hr. 5% aqueous sodium bicarbonate (50 mL) was added to the reaction mixture slowly and extracted with ethyl acetate (2×50 mL). Ethyl acetate layer was dried over anhydrous $Na_2SO_4$ and evaporated to dryness. Residue placed on a flash column and eluted with 10% MeOH in $CH_2Cl_2$ to givet the title compound (6.46 g, 72% yield). MS (Electrospray⁻) m/e 802 ($M-H^\oplus$)

EXAMPLE 77

2'-O-[(2-phthalimidoxy)ethyl]-3',5'-bis (tert butyldiphenylsilyl)guanosine

2'-O-(2-hydroxyethyl)-3',5'-bis (tert-butyldiphenylsilyl) guanosine (3.7 g, 4.61 mmol) was mixed with $Ph_3P$ (1.40 g, 5.35 mmol), and hydroxy phthalimide (0.87 g, 5.35 mmol). It was then dried over $P_2O_5$ under high vacuum for two days at 40° C. These anhydrous THF (46.1 mmol) was added to get a clear solution under inert atmosphere. Diethylazidocarboxylate (0.73 mL, 4.61 mmol) was added dropwise in such a manner that red color disappears before addition of the next drop. Resulting solution was then stirred at room temperature for 4 hr. THF was removed under vacuum and the residue dissolved in ethyl acetate (75 mL) and washed with water (2×50 mL). Ethyl acetate layer was dried over anhydrous $Na_2SO_4$ and concentrated to dryness. Residue was purified by column chromatography and eluted with 7% MeOH in ethyl acetate to give the title compound (2.62 g, 60% yield). Rf 0.48 (10% MeOH in $CH_2Cl_2$). MS (FAB⁻) m/e 947 ($M-H^\oplus$).

EXAMPLE 78

5'-O-DMT-2'-O—(N,N-dimethylaminooxyethyl)-N-2-isobutyrylguanosine-3'-O-phosphoramidite 2'-O-(2-phthalimido-N-oxyethyl)-3',5'-O-bis-tert-butyldiphenylsilyl guanosine (3.66 g, 3.86 mmol) was dissolved in anhydrous pyridine (40 mL), the solution was cooled to 5° C., and isobutyryl chloride (0.808 mL, 7.72 mmol) was added dropwise. The reaction mixture was allowed to warm to 25° C., and after 2 h additional isobutyryl chloride (0.40 mL, 3.35 mmol) was added at 25° C. After 1 h the solvent was evaporated in vaccuo (0.1 torr) at 30° C. to give a foam which was dissolved in ethyl acetate (150 mL) to give a fine suspension. The suspension was washed with water (2×15 mL) and brine (4 mL), and the organic layer was separated and dried over $MgSO_4$. The solvent was evaporated in vaccuo to give a foam, which was purified by column chromatography using $CH_2Cl_2$-MeOH, 94:6, v/v, to afford the 5'-O—, 3'-O—, and N2-protected nucleoside as a white foam (2.57 g, 65%).

¹H NMR(CDCl₃): d 11.97 (br s, 1H), 8.73 (s, 1H), 7.8–7.2 (m, 25H), 5.93 (d, 1H, $J_{1',2'}$=3.3 Hz), 4.46 (m, 1H), 4.24 (m, 2H), 3.83 (m, 2H), 3.60 (m, 2H), 3.32 (m, 1H), 2.67 (m, 1H), 1.30 (d, 3H, J=3.2 Hz), 1.26 (d, 3H, j=3.1 Hz), 1.05 (s, 9H), 1.02 (s, 9H)

The 5'-O—, 3'-O—, and N2-protected nucleoside was further derivatized into the corresponding phosphoramidite using the chemistries described above for the A and T analogs to give the title compound.

EXAMPLE 79

3'-O-acetyl-2'-O-(2-N,N-dimethylaminooxyethyl)-5'-O-tert-butyldiphenylsilyl thymidine 5'-O-tert-butyldiphenylsilyl-2'-O-[N,N-dimethylaminooxyethyl]-5-methyluridine (3.04 g, 5.21 mmol) was dissolved in chloroform (11.4 mL). To this was added dimethylaminopyridine (0.99 g, 8.10 mmol) and the reaction mixture was stirred for 10 minutes. Acetic anhydride (0.701 g, 6.87 mmol) was added and the reaction mixture was stirred overnight. The reaction mixture was then diluted with $CH_2Cl_2$ (40 mL) and washed with saturated $NaHCO_3$ (30 mL) and brine. (30 mL). $CH_2Cl_2$ layer evaporated to dryness. Residue placed on a flash column and eluted with ethyl, acetate:hexane (80:20) to yield the title compound. Rf 0.43 (ethyl acetate:hexane, 80:20). MS (Electrospray) m/e 624 ($M-H^\oplus$).

EXAMPLE 80

2'-O-(2-N,N-dimethylaminooxyethyl)-5'-O-tert-butyldiphenylsilyl 5-methyl cytidine A suspension of 1,2,4-triazole (5.86 g, 84.83 mmol) in anhydrous $CH_3CN$ (49 mL) was cooled in an ice bath for 5 to 10 min. under argon atmosphere. To this cold suspension $POCl_3$ (1.87 mL, 20 mmol) was added slowly over 10 min. and stirring continued for an additional 5 min. Triethylamine (13.91 mL, 99.8 mmol) was added slowly over 30 min., keeping the bath temperature around 0–2° C. After the addition was complete the reaction mixture was stirred at this temperature for an additional 30 minutes when N-1-Hydroxy phthalimido-5-O-(cyanoethoxydiisopropylaminophosphoroamidite)-6-O-dimethyoxytrityl-5,6 hexane-diol (3.12 g, 4.99 mmol) was added in anhydrous acetonitrile (3 mL) in one portion. The reaction mixture was stirred at 0–2° C. for 10 min. Then ice bath was removed and the reaction mixture was stirred at room temperature for 1.5 hr. The reaction mixture was cooled to ° C. and this was concentrated to smaller volume and dissolved in ethyl acetate (100 mL), washed with water (2×30 mL) and brine (30 mL). Organic layer was dried over anhydrous $Na_2SO_4$ and concentrated to dryness. Residue obtained was then dissolved in saturated solution of $NH_3$ in dioxane (25 mL) and stirred at room temperature overnight. Solvent was removed under vacuum. The residue was purified by column chromatography and eluted with 10% MeOH in $CH_2Cl_2$ to give the title compound.

EXAMPLE 81

2'-O-(2,N,N-dimethylaminooxyethyl)-$N^4$-benzoyl-5'-O-tert-butyldiphenylsilylcytidine 2'-O-(2-N,N-dimethylaminooxyethyl)-5'-O-tert-butyldiphenylsilyl 5-methyl cytidine (2.8 g, 4.81 mmol) was dissolved in anhydrous DMF (12.33 mL). Benzoic anhydride (1.4 g, 6.17 mmol) was added and the reaction mixture was stirred at room temperature overnight. Methanol was added (1 mL) and solvent evaporated to dryness. Residue was dissolved in dichloromethane (50 mL) and washed with saturated solution of $NaHCO_3$ (2×30 mL) followed by brine (30 mL). Dichloromethane layer was dried over anhydrous $Na_2SO_4$ and concentrated. The residue obtained was purified by column chromatography and eluted with 5% MeOH in $CH_2Cl_2$ to give the title compound as a foam.

EXAMPLE 82

$N^4$-Benzoyl-2'-O-(2-N,N-dimethylaminooxyethyl)-5-methyl cytidine

2'-O-(2,N,N-dimethylaminooxyethyl)-$N^4$-benzoyl-5'-O-tert-butyldiphenylsilylcytidine (2.5 g, 3.9 mmol) was dried over $P_2O_5$ under high vacuum. In a 100 mL round bottom flask, triethylamine trihydrofluoride (6.36 mL, 39 mmol) is dissolved in anhydrous THF (39 mL). To this, triethylamine (2.72 mL, 19.5 mmol) was added and the mixture was quickly poured into 2'-O-(2,N,N-dimethylaminooxyethyl)-$N^4$-benzoyl-5'-O-tert-butyldiphenylsilylcytidine and stirred at room temperature overnight. Solvent is removed under vacuum and the residue kept in a flash column and eluted with 10% MeOH in $CH_2Cl_2$ to give the title compound.

EXAMPLE 83

$N^4$-Benzoyl-2'-O-(2-N,N-dimethylaminooxyethyl)-5-O'-dimetoxytrityl-5-methyl cytidine $N^4$-Benzoyl-2'-O-(2-N,N-dimethylaminooxyethyl)-5-methyl cytidine (1.3 g, 2.98 mmol) was dried over $P_2O_5$ under high vacuum overnight. It was then co-evaporated with anhydrous pyridine (10 mL). Residue was dissolved in anhydrous pyridine (15 mL), 4-dimethylamino pyridine (10.9 mg, 0.3 mmol) was added and the solution was stirred at room temperature under argon atmosphere for 4 hr. Pyridine was removed under vacuum and the residue dissolved in ethyl acetate and washed with 5% $NaHCO_3$ (20 mL) and brine (20 mL). Ethyl acetate layer was dried over anhydrous $Na_2SO_4$ and concentrated to dryness. Residue was placed on a flash column and eluted with 10% MeOH in $CH_2Cl_2$ containing a few drops of pyridine to give the title compound.

EXAMPLE 84

$N^4$-Benzoyl-2'-O-(2-N,N-dimethylaminooxyethyl)-5-dimethoxytrityl-5-methyl cytidine-3'-O-phosphoramidite $N^4$-Benzoyl-2'-O-(2-N,N-dimethylaminooxyethyl)-5-O'-dimetoxytrityl-5-methyl cytidine(1.54 g, 2.09 mmol) was co-evaporated with toluene (10 mL). It was then mixed with diisopropylamine tetrazolide (0.36 g, 2.09 mmol) and dried over $P_2O_5$ under high vacuum at 40° C. overnight. Then it was dissolved in anhydrous acetonitrile (11 mL) and 2-cyanoethyl-tetraisopropylphosphoramidite (2.66 mL, 8.36 mmol) was added.

The reaction mixture was stirred at room temperature under inert atmosphere for 4 hr. Solvent was removed under vacuum. Ethyl acetate (50 mL) was added to the residue and washed with 5% $NaHCO_3$ (30 mL) and brine (30 mL). Organic phase was dried over anhydrous $Na_2SO_4$ and concentrated to dryness. Residue placed on a flash column and eluted with ethylacetate:hexane (60:40) containing a few drops of pyridine to give the title compound.

EXAMPLE 85

2'-O-dimethylaminooxyethyl-2,6-diaminopurine riboside phosphoramidite

For the incorporation of 2'-O-dimethylaminooxyethyl-2,6-diaminopurine riboside into oligonucleotides, we elected to use the phosphoramidite of protected 6-amino-2-fluoropurine riboside. Post-oligo synthesis, concomitant with the deprotection of oligonucleotide protection groups, the 2-fluoro group is displaced with ammonia to give the 2,6-diaminopurine riboside analog. Thus, 2,6-diaminopurine riboside is alkylated with dimethylaminooxyethylbromide to afford a mixture of 2'-O-dimethylaminooxyethyl-2,6-diaminopurine riboside and the 3'-isomer. Typically after functionalizing the 5'-hydroxyl with DMT to provide 5'-O-(4,4'-dimethoxytrityl)-2'-O-dimethylaminooxyethyl-2,6-diaminopurine riboside, the 2'-isomer is resolved chromatographically. Fluorination via the Schiemann reaction (Krolikiewicz, K.; Vorbruggen, H. Nucleosides Nucleotides, 1994, 13, 673–678) provides 2'-O-dimethylaminooxyethyl-6-amino-2-fluoro-purine riboside and standard protection protocols affords 5'-O-(4,4'-dimethoxytrityl)-2'-O-dimethylaminooxyethyl-6-dimethylformamide-2-fluoropurine riboside. Phosphitylation gives 5'-O-(4,4'-dimethoxytrityl)-2'-O-dimethylaminooxyethyl-6-dimethylformamide-2-fluoropurine riboside-3'-[(2-cyanoethyl)-N,N-diisopropylphosphoramidite].

In the event that amidite cannot be resolved chromatographically from the 3'-isomer, the mixture may be treated with adenosine deaminase, which is known to selectively deaminate 2'-O-substituted adenosine analogs in preference to the 3'-O-isomer, to afford 2'-O-dimethylaminooxyethylguanosine. 5'-O-(4,4'-dimethoxytrityl)-2'-O-dimethylaminooxyethylguanosine may be converted to the 2,6-diaminopurine riboside analog by amination of the 6-oxo group (Gryaznov, S.; Schultz, R. G. Tetrahedron Lett. 1994, 2489–2492). This is then converted to the corresponding amidite by standard protection methods and protocols for phosphitylation.

EXAMPLE 86

2'/3'-O-[2-(tert-butyldimethylsilylhydroxy) ethyl]-2,6-diaminopurine riboside 2,6-diaminopurine riboside (10 g, 35.46 mmol) was dried over $P_2O_5$ under high vacuum. It was suspended in anhydrous DMF (180 mL) and NaH (1.2 g, 35.46 mmol, 60% dispersion in mineral oil) was added. The reaction mixture was stirred at ambient temperature at inert atmosphere for 30 minutes. To this (2-bromoethoxy)-tert-butyldimethylsilane (12.73 g, 53.2 mmol) was added dropwise and the resulting solution was stirred at room temperature overnight. DMF was removed under vacuum, residue was dissolved in ethyl acetate (100 mL) and washed with water (2×70 mL). Ethyl acetate layer was dried over anhydrous $MgSO_4$ and concentrated to dryness. Residue was placed on a flash column and eluted with 5% MeOH in $CH_2Cl_2$ to get the title mixture of products (6.0711 g, 31% yield). Rf 0.49, 0.59, 0.68 (5% MeOH in $CH_2Cl_2$)

EXAMPLE 87

2'-O-aminooxyethyl analogs

Various other 2'-O-aminooxyethyl analogs of nucleoside (for e.g., 2,6-diaminopurine riboside) may be prepared as illustrated above. Thus, alkylation of 2,6-diamino purine with (2-bromoethoxy)-tert-butyldimethylsilane gives 2'-O-tert-butyldimethylsilyloxyethyl-2,6-diaminopurine riboside and the 3'-isomer. The desired 2'-O-isomer is resolved by preparation of 5'-O-(4,4'-dimethoxytrityl)-2'-O-tert-butyldimethylsilyloxyethyl-2,6-diaminopurine riboside and subjecting the mixture to column chromatography. Deprotection of the silyl group provides 5'-O-(4,4'-dimethoxytrityl)-2'-O-hydroxyethyl-2,6-diaminopurine riboside which undergoes a Mitsunobu reaction to give 5'-O-(4,4'-dimethoxytrityl)-2'-O-(2-phthalimido-N-oxyethyl)-2,6-diaminopurine riboside. Treatment under Schiemann conditions effects fluorination and deprotection of the DMT group to yield 2'-O-(2-phthalimido-N-oxyethyl)-6-amino-2-fluoropurine riboside. Standard protection conditions provides 5'-O-(4,4'-dimethoxytrityl)-2'-O-(2-phthalimido-N-oxyethyl)-6-dimethylformamide-2-fluoropurine riboside and deprotection of the phthalimido function affords 5'-O-(4,4'-dimethoxytrityl)-2'-O-aminooxyethyl-6-dimethylformamide-2-fluoropurine riboside.

Reductive amination of 5'-O-(4,4'-dimethoxytrityl)-2'-O-aminooxyethyl-6-dimethylformamide-2-fluoropurine riboside with aldehydes or dialdehydes results in cyclic or acyclic disubstituted 2'-O-aminooxyethyl analogs. Phosphitylation provides cyclic or acyclic disubstituted 2'-O-aminooxyethyl analogs as phosphoramidites.

EXAMPLE 88

2'/3'-O (2-tert-butyldimethylsilylhydroxyethyl) adenosine

Adenosine (10 g, 37.42 mmol) was dried over $P_2O_5$ under high vacuum. It was then suspended in anhydrous DMF (150 mL) and NaH (1.35 g, 56.13 mmol) was added. The reaction mixture was stirred at room temperature under inert atmosphere for 30 min. Then (2-bromo ethyl)-tert-butyldimethylsilane (9.68 mL, 4.4.90 mmol) was added dropwise and the reaction mixture stirred at room temperature overnight. DMF was removed under vacuum and to the residue dichloromethane (100 mL) was added and washed with water (2×80 mL). Dichloromethane layer was dried over anhydrous $Na_2SO_4$ and evaporated to dryness. Residue purified by column to get a mixture of the title compounds (4.30 g). Rf 0.49, 0.57 (10% MeOH in $CH_2Cl_2$)

EXAMPLE 89

2'-O-(2-methyleneiminooxyethyl)thymidine

In a 100 mL round bottom flask, triethylamine-trihydroflouride (8.93 mL, 54.8 mmol) was dissolved in anhydrous THF and triethylamine (3.82 mL, 27.4 mmol) was added to form a solution. This solution was added to 5'-O-tert-butyldiphenylsilyl-2'-O-[(2-formadoximinooxy)ethyl]-5-methyluridine (3.10 g, 5.48 mmol) that had been dried over $P_2O_5$ under high vacuum and the reaction mixture was stirred at room temperature overnight. Solvent was removed under vacuum. Residue obtained was placed on a flash column and eluted with 10% MeOH in $CH_2Cl_2$ to give the title compound as white foam (1.35 g, 75% yield). Rf 0.45 (5% MeOH in $CH_2Cl_2$) MS (FAB$^⊕$) m/e 330 (M+H$^⊕$), 352 (M+Na$^⊕$)

EXAMPLE 90

5'-O-dimethoxytrityl-2'-O-(2-methyleneiminooxyethyl)thymidine

2'-O-(2-methyleneiminooxyethyl) thymidine (0.64 g, 1.95 mmol) was dried over $P_2O_5$ under high vacuum overnight. It was then co-evaporated with anhydrous pyridine (5 mL). Residue dissolved in anhydrous pyridine (4.43 mL) and dimethoxytrityl chloride (0.79 g, 2.34 mmol), and 4-dimethylaminopyridine (23.8 mg, 0.2 mmol) was added. Reaction mixture was stirred under inert atmosphere at ambient temperature for 4 hrs. Solvent was removed under vacuum, the residue purified by column and eluted with 5% MeOH in $CH_2Cl_2$ containing a few drops of pyridine to give the title compound as a foam (1.09 g, 88% yield). Rf 0.4 (5% MeOH in $CH_2Cl_2$). MS (Electrospray$^-$) m/e 630 (M–H$^⊕$).

EXAMPLE 91

5'-O-dimethoxytrityl-2'-O-(2-methyleneiminooxyethyl)thymidine-3'-O-phosphoramidite 5'-O-dimethoxytrityl-2'-O-(2-methyleneiminooxyethyl) thymidine (0.879, 1.34 mmol) was co-evaporated with toluene (10 mL). Residue was then mixed with diisopropylamine tetrazolide (0.23 g, 1.34 mmol) and dried over $P_2O_5$ under high vacuum overnight. It was then flushed with argon. Anhydrous acetonitrile (6.7 mL) was added to get a clear solution. To this solution 2-cyanoethyl tetraisopropylphosphorodiamidites (1.7 mL, 5.36 mmol) was added and the reaction mixture was stirred at room temperature for 6 hr. under inert atmosphere. Solvent was removed under vacuum, the residue was diluted with ethyl acetate (40 mL), and washed with 5% $NaHCO_3$ (20 mL) and brine (20 mL). Ethyl acetate layer was dried over anhydrous $Na_2SO_4$ and concentrated to dryness. Residue placed on a flash column and eluted with ethyl acetate:hexane (60:40) to give the title compound (1.92 g, 80% yield). Rf 0.34 (ethyl acetate:hexane, 60:40). $^{31}P$ NMR (CDCl$_3$) δ 150.76 ppm, MS (Electrospray$^-$) m/e 830 (M–H$^⊕$).

EXAMPLE 92

Attachment of a Nucleoside to Solid Support General Procedure

5'-O-DMT-2'-O-(dimethylaminooxyethyl)-5-methyluridine (200 mg, 0.31 mmol) was mixed with DMAP (19 mg, 16 mmol), succinic anhydride (47 mg, 0.47 mmol), triethylamine (86 mL, 0.62 mmol) and dichloromethane (0.8 mL) and stirred for 4 hr. The mixture was diluted with $CH_2Cl_2$ (50 mL) and the $CH_2Cl_2$ layer was washed first with ice cold 10% aqueous citric acid and then with water. The organic phase was concentrated to dryness to give the nucleoside bound to the solid support through a succinyl linker at the 3'-O— group. The solid support bound material was dissolved in anhydrous acetonitrile (23 mL). To this DMAP (37 mg, 0.3 mmol), and 2',2'-dithiobis(5-nitropyridine) (103 mg, 0.33 mmol) were added. The solution was stirred for 5 min. To this was added triphenylphosphine (78.69 mg, 0.3 mmol) in anhydrous acetonitrile (3 mL). The solution was stirred for 10 min. and then CPG was added to it. The slurry was then shaken for 2 hr. It was then filtered, washed with acetonitrile and $CH_2Cl_2$. The functionalized CPG was dried and capped with capping solution to give the solid support bound 2'—O— modified nucleoside. Loading capacity was determined (58.3 μmol/g).

EXAMPLE 93
Synthesis of Aminooxy Derivatives: Alternative Procedure

5'-O-dimethoxytrityl-2'-O-hydroxyethyl thymidine is converted to the 2'-O-(O-tosyl)hydroxyethyl derivative by treatment with 1 equivalent of p-toluenesulfonyl chloride-pyridine followed by standard work-up. The tosylate is subsequently treated with several amino-hydroxy compounds to act as nucleophils in displacing tosylate to yield a series of oxy-amino compounds. The reaction is facilitated by preforming the anion from the amino alcohol or hydroxylamine derivative by the use of sodium hydride under anhydrous conditions.

EXAMPLE 94
Oligomer Synthesis

Solid support bound 2'-O-methyl-5-methyl-5'-O-DMT-uridine attached to solid support through the 3'-O— is purchased from ChemGenes. The 5'-O-DMT blocking group is removed as per standard protocols. The solid support bound material is coupled via oxidative phosphorylation to the product of Example 27 to give a modified dimer in a protected form. The modified dimer can be elongated by addition of nucleosides and or nucleotides. Additional modified dimers are added by coupling the product of Example 28 followed by the coupling of the product of Example 27. The TBDPS groups are removed by treatment with F$^-$.

EXAMPLE 95
General Procedure for the Synthesis of Oligonucleotides and Oligonucleotide Analogs The synthesis of oligonucleotides and oligonucleotide analogs was by standard automated synthesis using standard reagents and methods. Phosphoramidites (0.1 M) in anhydrous acetonitrile were employed in 1 μmol scale syntheses following standard protocol for DNA synthesis. The coupling of modified dimers such as the MMI dimer 3'-de(oxyphosphinico)-3'-(methyleneimino)-5'-DMT-2'-O-acetyl-5-methyluridylyl(3>5)-2'-O-methyl-5-methyluridine-3'-phosphoramidite (TT$^1$ above), was allowed to proceed for 15 minutes on the synthesizer and the process was repeated three times. (1S)-(+)-10-(camphorsulfonyl)oxaziridine was used as the oxidizer. oligonucleotide analogs were synthesized as 5'-O-DMT derivatives. They were cleaved from solid support, base-deprotected and 2'-O-deacetylated by incubation in 30% aqueous ammonia overnight at 55° C. The resulting crude material was purified by reverse-phase HPLC on C-18 column with 50 mM triethylammonium acetate and acetonitrile as eluents utilizing a gradient from 5 to 60% acetonitrile in 60 minutes and a flow rate of 2.5 mL/minute. Cleavage of 5'-O-DMT in 80% aqueous AcOH at room temperature in 0.5 hour was followed by size-exclusion chromatography on G-25 column. The characterization and purity of the isolated oligonucleotide analogs was determined by HPLC, CE and ES MS (See Table).

EXAMPLE 96
Enhanced Binding Affinity of Compounds of the Invention

To illustrate the enhanced affinity for complementary RNA shown by compounds of the invention, oligonucleotide analogs were synthesized having from 1 to 5 modified dimers incorporated therrein. Backbone linkages of the oligonucleotide analogs assayed were phosphodiester except for the linkages in each individual modified dimers which were MMI (the dimer structures are shown below). Dimers that are joined to other dimers in a sequence were joined by phosphodiester linkages. A DNA sequence was also prepared for each of the 3 sequences being used in the study. The thermal melt of each of the oligonucleotide analogs shown below was measured against RNA, as was the corresponding DNA sequence. Comparison of the $T_m$'s of each oligonucleotide analog with its corresponding DNA sequence gave the $\Delta T_m$ values below in Table I.

TABLE I

| SEQ ID NO: | Sequence | | | | | | | | $\Delta T_m$/mod |
|---|---|---|---|---|---|---|---|---|---|
| 1 | CTC | GTA | CC | TT$^1$ | | TC | CGG | TCC | 2.26 |
| 2 | CTC | GTA | CC | TT$^2$ | | TC | CGG | TCC | 1.85 |
| 3 | CTC | GTA | CC | TT$^3$ | | TC | CGG | TCC | 1.51 |
| 4 | CTC | GTA | C | TT$^1$ | TT$^1$ | C | CGG | TCC | 3.19 |
| 5 | CTC | GTA | C | TT$^2$ | TT$^2$ | C | CGG | TCC | 2.78 |
| 6 | CTC | GTA | C | TT$^3$ | TT$^3$ | C | CGG | TCC | -0.23 |
| 7 | GCG | TT$^1$ | TT$^1$ | TT$^1$ | TT$^1$ | TT$^1$ | GC | G | 3.83 |
| 8 | GCG | TT$^2$ | TT$^2$ | TT$^2$ | TT$^2$ | TT$^2$ | GC | G | 3.80 |
| 9 | GCG | TT$^3$ | TT$^3$ | TT$^3$ | TT$^3$ | TT$^3$ | GC | G | 0.13 |

TT$^1$

TT$^2$

TT$^3$

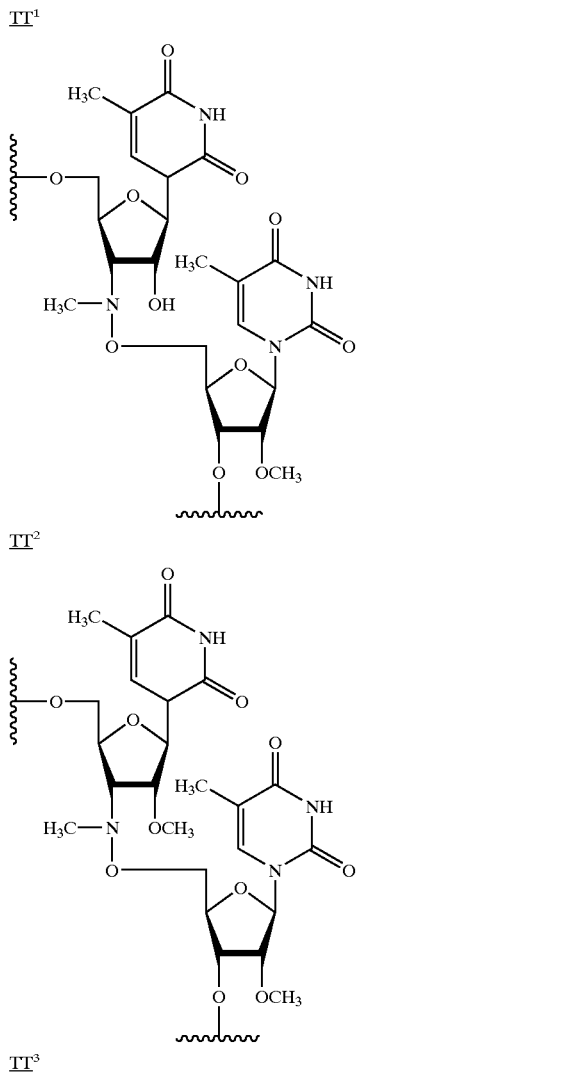

TABLE I-continued

| SEQ ID NO: | Sequence | $\Delta T_m$/mod |
|---|---|---|

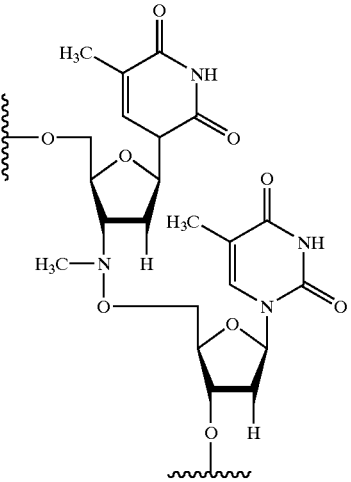

The highest $\Delta T_m$ values were seen with oligonucleotide analogs incorporating modified dimers having the combination of an unmodified ribose moiety in the 5' nucleoside and a 2'-O—$CH_3$ group attached to the ribose moiety in the 3' nucleoside ($TT^1$). In comparison, the 2',2"-O-bis-methoxy modified dimer ($TT^2$) showed an increased $T_m$ compared to DNA, but not as high as the $TT^1$ dimer. The ribose unmodified dimer ($TT^3$) showed a reduced affinity compared to its complementary DNA analog.

Procedure 1

Nuclease Resistance

A. Evaluation of the Resistance of Oligonucleotide Analogs to Serum and Cytoplasmic Nucleases.

Oligonucleotides including oligonucleotide analogs of the invention can be assessed for their resistance to serum nucleases by incubation in media containing various concentrations of fetal calf serum or adult human serum. Labeled oligonucleotides are incubated for various times, treated with protease K and then analyzed by gel electrophoresis on 20% polyacrylamide-urea denaturing gels and subsequent autoradiography. Autoradiograms are quantitated by laser densitometry. Based upon the location of the modifications and the known length of the oligonucleotide it is possible to determine the effect on nuclease degradation by the particular modification. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified and modified oligonucleotides. As a control, unsubstituted phosphodiester oligonucleotide have been found to be 50% degraded within 1 hour, and 100% degraded within 20 hours.

B. Evaluation of the Resistance of Oligonucleotide Analogs to Specific Endo- and Exonucleases Evaluation of the resistance of naturaly occurring and non-naturally occurring oligonucleotides including oligonucleotide analogs of the invention to specific nucleases (i.e., endonucleases, 3',5'-exo-, and 5',3'-exonucleases) is done to determine the exact effect on degradation. Oligonucleotide analogs are incubated in defined reaction buffers specific for various selected nucleases. Following treatment of the products with protease K, urea is added and analysis on 20% polyacrylamide gels containing urea is done. Gel products are visualized by staining using Stains All (Sigma Chemical Co.). Laser densitometry is used to quantitate the extend of degradation. The effects of the modifications are determined for specific nucleases and compared with the results obtained from the serum and cytoplasmic systems.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having Formula:

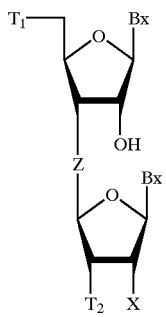

wherein:
Z is a phosphodiester or phosphorothioate intersugar linkage;
each $T_1$ and $T_2$ is, independently, —OH, —OR$_1$, —CH$_2$R$_1$, —NH(R$_1$), —SH, —SR$_1$, or a blocked hydroxyl;
$R_1$ is $C_1$-$C_{12}$ alkyl;
$B_X$ is a heterocyclic base; and
X is F, —OCH$_2$CH$_2$OCH$_3$ or —OCH$_2$CH$_2$CH$_2$NH$_2$ when Z is a phosporothioate intersugar linkage or X is —OCH$_2$CH$_2$OCH$_3$ or —OCH$_2$CH$_2$CH$_2$NH$_2$ when Z is a phosphodiester intersugar linkage.

2. The compound of claim 1 wherein X is —OCH$_2$CH$_2$OCH$_3$ or —OCH$_2$CH$_2$CH$_2$NH$_2$.

3. The compound of claim 2 wherein X is —O—CH$_2$—CH$_2$—O—CH$_3$.

4. An oligonucleotide analog comprising at least one moiety having Formula:

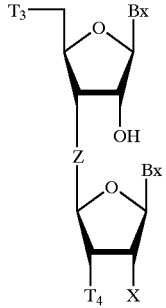

wherein
each Z is a phosphodiester or phosphorothioate intersugar linkage;
$T_3$ is a nucleotide other than a ribonucleotide, a nucleoside other than a ribonucleoside, a hydroxyl, a blocked hydroxyl, or an oligonucleotide wherein the 3'-terminal nucleotide of said oligonucleotide is not a ribonucleotide;
$T_4$ is a nucleotide, a nucleoside, an oligonucleotide, a hydroxyl or a blocked hydroxyl;
with the proviso that at least one of said $T_3$ and $T_4$ is not a hydroxyl, or blocked hydroxyl;
$B_X$ is a heterocyclic base; and
each X is F, OCH$_3$, —OCH$_2$CH$_2$OCH$_3$ or —OCH$_2$CH$_2$CH$_2$NH$_2$.

5. The oligonucleotide analog of claim wherein at least one X is OCH$_3$, —OCH$_2$CH$_2$OCH$_3$ or —OCH$_2$CH$_2$CH$_2$NH$_2$.

6. The oligonucleotide analog of claim 5 wherein X is OCH$_3$.

7. The oligonucleotide analog of claim 5 wherein X is —O—CH$_2$—CH$_2$—O—CH$_3$.

8. The oligonucleotide analog of claim 4 having a length of from 1 to 200 subunits.

9. The oligonucleotide analog of claim 4 having a length of from 10 to 25 subunits.

10. The oligonucleotide analog of claim 4 having a length of from 12 to 20 subunits.

11. A compound comprising a moiety of Formula:

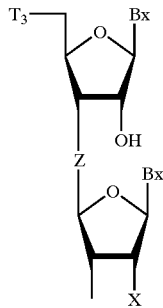

wherein:
Z is a phosphodiester or phosphorothioate intersugar linkage;
$B_X$ is a heterocyclic base; and
X is F, —OCH$_3$, —OCH$_2$CH$_2$OCH$_3$ or —OCH$_2$CH$_2$CH$_2$NH$_2$ when Z is a phosporothioate intersugar linkage or X is OCH$_3$, —OCH$_2$CH$_2$OCH$_3$ or —OCH$_2$CH$_2$CH$_2$NH$_2$ when Z is a phosphodiester intersugar linkage; and
$T_3$ is a nucleotide, a nucleoside, an oligonucleotide, a hydroxyl or a blocked hydroxyl, wherein said nucleotide is not a ribonucleotide, and said nucleoside is not a ribonucleoside, and wherein the 3'-terminal nucleotide of said oligonucleotide is not a ribonucleotide.

12. The compound of claim 11 wherein X is —OCH$_3$, —OCH$_2$CH$_2$OCH$_3$ or —OCH$_2$CH$_2$CH$_2$NH$_2$.

13. The compound of claim 12 wherein X is —OCH$_3$.

14. The compound of claim 12 wherein X is —O—CH$_2$—CH$_2$—O—CH$_3$.

* * * * *

UNITED STATES PATENT AND TRADEMARK OFFICE
CERTIFICATE OF CORRECTION

PATENT NO. : 6,849,723 B2
DATED : February 1, 2005
INVENTOR(S) : Phillip Dan Cook et al.

It is certified that error appears in the above-identified patent and that said Letters Patent is hereby corrected as shown below:

<u>Column 60,</u>
Line 7, insert -- 4 -- between "claim" and "wherein".

Signed and Sealed this

Sixteenth Day of May, 2006

JON W. DUDAS
*Director of the United States Patent and Trademark Office*